United States Patent
Deng et al.

(10) Patent No.: US 10,272,019 B2
(45) Date of Patent: *Apr. 30, 2019

(54) TOPICAL FORMULATION OF HYPERBRANCHED POLYGLYCEROL-COATED PARTICLES THEREOF

(71) Applicant: Yale University, New Haven, CT (US)

(72) Inventors: Yang Deng, New Haven, CT (US); Asiri Ediriwickrema, Cary, NC (US); William M. Saltzman, New Haven, CT (US)

(73) Assignee: Yale University, New Haven, CT (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/309,733

(22) PCT Filed: May 11, 2015

(86) PCT No.: PCT/US2015/030187

§ 371 (c)(1),
(2) Date: Nov. 8, 2016

(87) PCT Pub. No.: WO2015/172153

PCT Pub. Date: Nov. 12, 2015

(65) Prior Publication Data

US 2018/0177688 A1     Jun. 28, 2018

Related U.S. Application Data

(60) Provisional application No. 61/991,025, filed on May 9, 2014.

(51) Int. Cl.
*A61K 8/02*     (2006.01)
*C08G 83/00*     (2006.01)
(Continued)

(52) U.S. Cl.
CPC .............. *A61K 8/0241* (2013.01); *A61K 8/90* (2013.01); *A61K 9/0014* (2013.01);
(Continued)

(58) Field of Classification Search
CPC .. A61K 8/0241; A61K 9/5153; A61K 9/1647; A61K 2800/433; A61Q 17/04
See application file for complete search history.

(56) References Cited

U.S. PATENT DOCUMENTS 8,715,736 B2 *    5/2014   Sachdeva ............. A61K 31/192
                                                                                               424/489

FOREIGN PATENT DOCUMENTS

WO         2012156094      11/2012

OTHER PUBLICATIONS

Gao et al, "Synthesis and Physicochemical Characterization of a Novel Amphiphilic Polylactic Acid-Hyperbranched Polyglycerol for Protein Delivery", Journal of Controlled Release, 2009, vol. 140, pp. 141-147.*

(Continued)

*Primary Examiner* — Carlos A Azpuru
(74) *Attorney, Agent, or Firm* — Pabst Patent Group LLP

(57) ABSTRACT

Core-shell particles have a hydrophobic core and a shell formed of or containing hyperbranched polyglycerol (HPG). The HPG can be covalently bound to the one or more materials that form the core or coated thereon. The HPG coating can be modified to adjust the properties of the particles. For example, unmodified HPG coatings impart stealth properties to the particles which resist non-specific protein absorption. Alternatively, the hydroxyl groups on the HPG coating can be chemically modified to form functional groups that react with functional groups on tissue or otherwise interact with tissue to adhere the particles to the tissue, cells, or extracellular materials, such as proteins. Such (Continued)

functional groups include, but not limited to, aldehydes, amines, and O-substituted oximes. Topical formulation for application to the skin contain these HPG coated nanoparticles. In some embodiments, the particles include therapeutic, diagnostic, nutraceutical, and/or prophylactic agents such as those used as sunblock compositions.

26 Claims, 8 Drawing Sheets

(51) Int. Cl.
| | |
|---|---|
| C07C 59/06 | (2006.01) |
| C07C 59/08 | (2006.01) |
| A61K 9/50 | (2006.01) |
| A61K 31/4178 | (2006.01) |
| A61K 9/16 | (2006.01) |
| A61K 31/427 | (2006.01) |
| A61K 9/00 | (2006.01) |
| A61K 9/51 | (2006.01) |
| A61K 31/4745 | (2006.01) |
| A61K 47/34 | (2017.01) |
| A61K 8/90 | (2006.01) |
| A61Q 17/04 | (2006.01) |

(52) U.S. Cl.
CPC .......... *A61K 9/0019* (2013.01); *A61K 9/0053* (2013.01); *A61K 9/1647* (2013.01); *A61K 9/5031* (2013.01); *A61K 9/5146* (2013.01); *A61K 9/5153* (2013.01); *A61K 31/4178* (2013.01); *A61K 31/427* (2013.01); *A61K 31/4745* (2013.01); *A61K 47/34* (2013.01); *A61Q 17/04* (2013.01); *C07C 59/06* (2013.01); *C07C 59/08* (2013.01); *C08G 83/005* (2013.01); *A61K 2800/412* (2013.01); *A61K 2800/413* (2013.01); *A61K 2800/624* (2013.01)

(56) References Cited

OTHER PUBLICATIONS

Bao, et al., "OX26 modified hyperbranched polyglycerol-conjugated poly(lactic-co-glycolic acid) nanoparticles: synthesis, characterization and evaluation of its brain delivery ability", J Mater Sci Mater Med., 23:1891-901 (2012).
Barnard, "One-to-one comparison of sunscreen efficacy, aesthetics and potential nanotoxicity", Nature Nanotech., 5:271-4 (2010).
Deng, et al., "The effect of hyperbranched polyglycerol coatings on drug delivery using degradable polymer nanoparticles", Biomaterials, 35:6595-602 (2014).
Gao, et al., "Synthesis and physicochemical characterization of a novel amphiphilic polylactic acid-hyperbranched polyglycerol conjugate for protein delivery", J Controled Release, 140:141-7 (2009).
Gu and Roy, "Topical permeation enhancers efficiently deliver polymer micro and nanoparticles to epidermal Langerhans' cells", J Drug Deliv Sci Tec., 14:265-73 (2004).
Gu, et al. "Precise engineering of targeted nanoparticles by using self-assembled biointegrated block copolymers", PNAS, 105:2586-91 (2008).
Hayden, et al., "Sunscreen penetration of human skin and related keratinocyte toxicity after topical application", Skin Pharmacol. Physiol. 18:170-4 (2005).
Kimura, et al., "Measurement of skin permeation/penetration of nanoparticles for their safety evaluation", Biol. Pharm. Bull. 35:1476-86 (2012).
Mitragotri, et al., "Overcoming the challenges in administering biopharmaceuticals: formulation and delivery strategies", Nature Reviews. Drug discovery, 13:655-72 (2014).
Perugini, et al., "Effect of nanoparticle encapsulation on the photostability of the sunscreen agent, 2-ethylhexyl-p-methoxycinnamate", Int J Pharma., 246:37-45 (2002).
Quatrano and Dinulos, "Current principles of sunscreen use in children", Curr. Opin. Pediatr. 25:122-9 (2013).
Tanner, "Sunscreen product formulation", Dermatologic Clinics, 24:53-62 (2006).
Vemula, et al., "Nanoparticles reduce nickel allergy by capturing metal ions.", Nature Nanotech., 6:291-5 (2011).
Yeh, et al., "Self-assembled monothiol-terminated hyperbranched polyglycerols on a gold surface: a comparative study on the structure, morphology, and protein adsorption characteristics with linear poly(ethylene glycol)s.", Langmuir. 24(9):4907-16(2008).
Zakrewsky, et al., "Ionic liquids as a class of materials for transdermal delivery and pathogen neutralization", PNAS., 111:13313-8 (2014).
Zheng, et al., "Topical delivery of siRNA-based spherical nucleic acid nanoparticle conjugates for gene regulation", PNAS, 109:11975-80 (2012).
International Search Report for corresponding PCT application PCT/US2015/030187 dated Aug. 5, 2015.

* cited by examiner

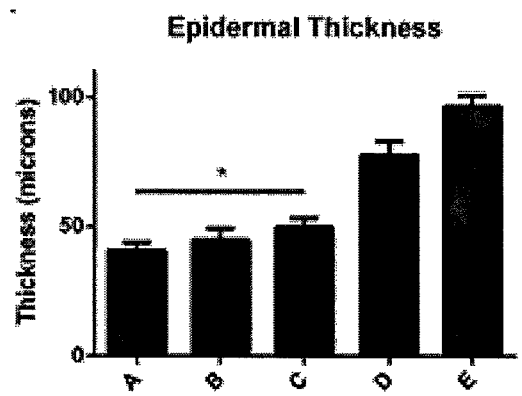
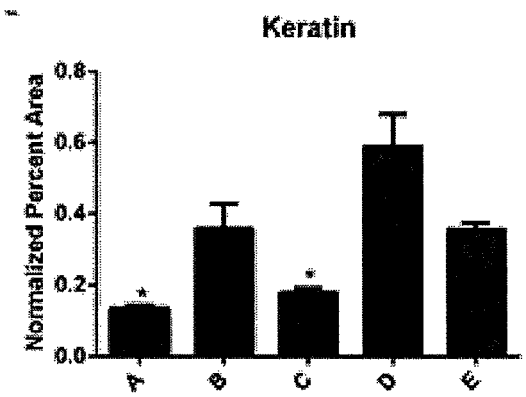
A) Normal Skin, B) Sunscreen, C) NP PO, D) NP Blank, E) No Treatment
FIG. 7A                                      FIG. 7B
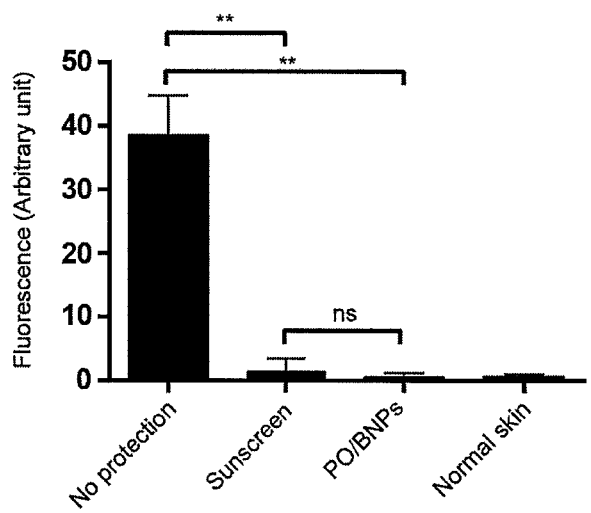
FIG. 8

TOPICAL FORMULATION OF HYPERBRANCHED POLYGLYCEROL-COATED PARTICLES THEREOF

CROSS REFERENCE TO RELATED APPLICATIONS

This application is a 371 application of International Application No. PCT/US2015/030187, filed May 11, 2016, which claims benefit of U.S. Provisional Application No. 61/991,025, filed May 9, 2014, which is incorporated herein by reference in its entirety.

STATEMENT REGARDING FEDERALLY SPONSORED RESEARCH

This invention was made with government support under Grant Nos. EB000487 and CA149128 awarded by the National Institutes of Health. The government has certain rights in the invention.

FIELD OF THE INVENTION

This invention is in the field of particles, such as microparticles and/or nanoparticles, coated with hyperbranched polyglycerol, wherein the coating can be tuned to provide stealth or adhesive properties.

BACKGROUND OF THE INVENTION

Ultraviolet (UV) radiation from sunlight can lead to multiple adverse effects including cutaneous phototoxicity (sunburn), photoaging, and carcinogenesis (Federman et al., *JAMA* 312:87-88 (2014); Stern et al, *Journal of the American Academy of Dermatology* 44:755-761 (2001)). UVB directly induces cyclopyrimidine dimers (CPDs) within the genomic DNA (gDNA) of keratinocytes, and both UVA and UVB exposure markedly enhance production of reactive oxidation species (ROS) that damage a variety of cellular components, including gDNA (Gilchrest, B. A. *The Journal of Investigative Dermatology* 133:E2-6 (2013)), and induce immunosuppressive cytokines (Schwarz and Luger, *Journal of Photochemistry and Photobiology. B, Biology* 4:1-13 (1989)). UV-exposure is clearly linked to both melanoma and non-melanoma skin cancer development (Gordon et al, *Facial Plastic Surgery: FPS* 29:402-410 (2013)). Over the past few decades, commercially available UV-protective sunblocks have largely incorporated organic UV filters [e.g. avobenzone, octinoxate, octocrylene, oxybenzone and padimate O (PO) (Hayden et al., *Skin Pharmacol. Physiol.* 18:170-174 (2005)] as formulations based on oil/water emulsions (Quatrano and Dinulos, *Curr. Opin. Pediatr.* 25:122-129 (2013)). There are substantial concerns, however, that these aromatic organic compounds can penetrate through the stratum corneum, or via follicles, into epidermal cells, keratinocytes and Langerhans cells (Hayden et al., *Skin Pharmacol. Physiol.* 18:170-174 (2005)). The potential for systemic absorption of such organic compounds, and their depot in adipose tissue, has also been a concern (Gulston and Knowland, *Mutat Res-Gen Tox En* 444:49-60 (1999); Hanson et al., *Free Radical Biology and Medicine* 41:1205-1212 (2006); Bastien et al., *The Journal of Investigative Dermatology*, 130:2463-2471 (2010); Krause et al., *Int. J. Androl.* 35:424-436 (2012)).

Alternatively, UV-blocking inorganic materials such as micronized zinc oxide (ZnO) and titanium dioxide ($TiO_2$) particles (Barnard, *Nature Nanotechnology*, 5:271-274 (2010)) have been utilized. While transdermal penetration of the inorganic particles appears to be less of a concern than for the organic agents, both types of sunblock agents have shown the capacity to enhance ROS generation after UV exposure, suggesting even small quantities may contribute to cellular damage and ultimately carcinogenesis (Pan et al., *Small*, 5:511-520 (2009); Trouiller et al., *Cancer Res.* 69:8784-8789 (2009); Wu et al., *Toxicology Letters*, 191:1-8 (2009); Zhang et al., *Journal of Biomedical Nanotechnology*, 10:1450-1457 (2014)). Thus, while the application of such products protects against sunburn, e.g. raises the skin's minimal erythema dose (MED), there continues to be controversy regarding their overall effectiveness in preventing skin cancer (Krause et al., *Int. J. Androl.* 35:424-436 (2012); Planta, *Journal of the American Board of Family Medicine: JABFM*, 24:735-739 (2011); Lindqvist et al., *J. Intern. Med.* 276:77-86 (2014); Plourde, E. Sunscreens—Biohazard: Treat As Hazardous Waste. (New Voice Publications (2011)). Moreover, several UV filters have been detected in human urine and breast milk samples after tropical treatment, and may mediate systemic effects including endocrine disruption (Hayden et al., *Skin Pharmacol. Physiol.* 18:170-174 (2005); Krause et al., *Int. J. Androl.* 35:424-436 (2012); Hayden et al., *Lancet*, 350:863-864 (1997)). Therefore, preventing direct skin contact and subsequent epidermal penetration may be essential to eliminating the potential adverse effects of sunscreens.

Some commercially available sunscreens are opaque, due to their use of large particles (Barnard, *Nature Nanotechnology*, 5:271-274 (2010)). The smaller, non-adhesive nanoparticles used in other commercially available sunscreens accumulate in hair follicles or penetrate deep into dermis, causing a variety of adverse effects (Vemula et al., *Nature Nanotechnology*, 6:291-295 (2011); Kimura et al., *Biol. Pharm. Bull.* 35:1476-1486 (2012)). Numerical simulations of nanoparticle properties suggest that unless small nanoparticles can be clearly demonstrated as safe, it is increasingly difficult to solve this paradox (Barnard, *Nature Nanotechnology*, 5:271-274 (2010)). (Mitragotri et al., *Nature Reviews. Drug discovery*, 13:655-672 (2014); Zakrewsky et al., *Proc. Natl. Acad. Sci. U.S.A.* 111:13313-13318 (2014); Zheng et al., *Proc. Natl. Acad. Sci. U.S.A.* 109:11975-11980 (2012); Gu and Roy, *J Drug Deliv Sci Tec.* 14:265-273 (2004)).

Commercial sunscreens polymerize monomers with an initiator in order to stabilize the UV filters into a film that coats the skin. The chemicals involved include a variety of acrylate derivatives and multiple initiators (Nair et al., *Pigment Cell and Melanoma Research* 27:843-845 (2014), which have been implicated in irritant and allergic contact dermatitis (Bennassar et al., *Dermatology Online Journal* 15:14 (2009); Rietschel, R. L. Fisher's Contact Dermatitis. (Pmph Usa; 6 edition (Apr. 2, 2007)).

It is therefore an object of the present invention to provide improved sunblock particles for use in sunscreens.

SUMMARY OF THE INVENTION

Core-shell particles, such as microparticles and nanoparticles, and methods of making and using thereof are described herein. The core is formed of or contains a hydrophobic material, preferably polymeric. The shell is formed of or contains hyperbranched polyglycerol (HPG). The HPG can be covalently bound to the one or more materials that form the core such that the hydrophilic HPG is oriented towards the outside of the particles and the hydrophobic material oriented to form the core.

The HPG coating can be modified to adjust the properties of the particles. For example, unmodified HPG coatings impart stealth properties to the particles which resist non-specific protein absorption. Alternatively, the hydroxyl groups on the HPG coating can be chemically modified to form functional groups that react with functional groups on tissue or otherwise interact with tissue to adhere the particles to the tissue, cells, or extracellular materials, such as proteins. Such functional groups include, but not limited to, aldehydes, amines, and O-substituted oximes.

Topical formulations for application to the skin contain these HPG coated nanoparticles. Nanoparticles with unusually strong bioadhesive properties do not diffuse into hair follicles and are useful as sunscreens or delivery of therapeutic, prophylactic, diagnostic or nutraceutical agents. In some embodiments, the adhesive particles include prophylactic agents, such as ultraviolet (UV) light filters. The particles are applied topically. They can be used as or formulated in a sunscreen. The nanoparticles are useful in other topical applications, such as transdermal delivery of therapeutic, diagnostic, nutraceutical and/or prophylactic agents.

BRIEF DESCRIPTION OF THE DRAWINGS

FIG. 7A is a bar graph showing epidermal thickness (microns) after receiving different topical interventions. FIG. 7B is a bar graph showing normalized percent area of keratin within the dorsal skin after receiving different interventions. The interventions were: A) Normal skin, B) Sunscreen, C) PO/PLA-HPG$_{ALD}$ NPs, D) blank PLA-HPG$_{ALD}$ NPs, and E) No treatment.

FIG. 8 is a bar graph showing fluorescence (arbitrary units) of cyclopyrimidine dimers (CPD) on skin that received different topical interventions. Data are shown as mean±SD (n=3), **p<0.01 (student t-test). PO/BNP—bioadnesive nanoparticles (PLA-HPG$_{ALD}$ NPs) encapsulating PO, PO—padamate O.

FIG. 10A is a diagram of sunscreen formulations applied onto the skin. FIG. 10B is a diagram of the skin after application: regular sunscreen penetrates into the skin whereas the PLA-HPG$_{ALD}$ NP (BNPs) formulation remains on the stratum corneum. FIG. 10C is a diagram of the skin after sunlight exposure: UV filters produce deleterious ROS, however, PLA-HPG$_{ALD}$ NPs (BNPs) do not penetrate into the skin and prevent ROS mediated toxicity by confining these toxic products within the particle. BNP—bioadhesive nanoparticles (PLA-HPG$_{ALD}$ NPs), UV—ultraviolet.

DETAILED DESCRIPTION OF THE INVENTION

I. Definitions

Figure 1A:
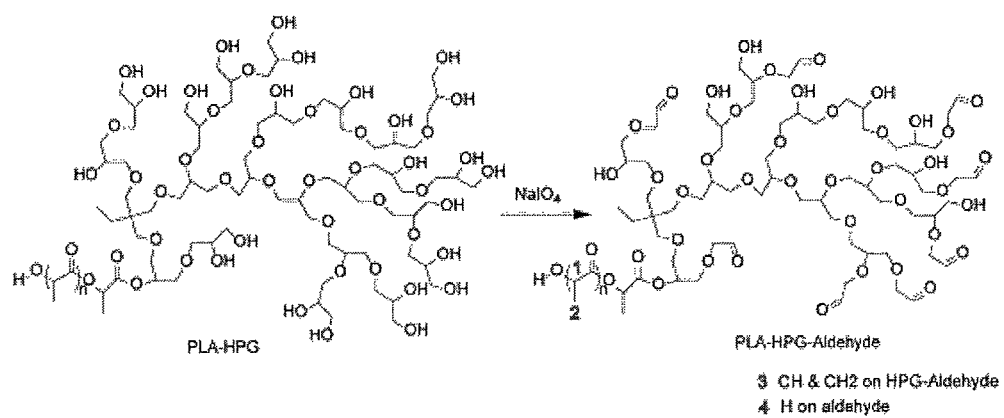
FIG. 1A is a schematic of bioadhesive PLA-HPG$_{ALD}$.

"Effective amount" or "therapeutically effective amount", as used herein, refers to an amount of drug effective to alleviate, delay onset of, or prevent one or more symptoms of a disease or disorder.

The terms "treating" or "preventing", as used herein, can include preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

"Topical administration", as used herein, means the non-invasive administration to the skin, orifices, or mucosa. Topical administrations can be administered locally, i.e. they are capable of providing a local effect in the region of application without systemic exposure. Topical formulations can provide systemic effect via adsorption into the blood stream of the individual. Topical administration can include, but is not limited to, cutaneous and transdermal administration, buccal administration, intranasal administration, intravaginal administration, intravesical administration, ophthalmic administration, and rectal administration.

The terms "bioactive agent" and "active agent", as used interchangeably herein, include, without limitation, physiologically or pharmacologically active substances that act locally or systemically in the body. A bioactive agent is a substance used for the treatment (e.g., therapeutic agent), prevention (e.g., prophylactic agent), diagnosis (e.g., diagnostic agent), cure or mitigation of disease or illness, a substance which affects the structure or function of the body, or pro-drugs, which become biologically active or more active after they have been placed in a predetermined physiological environment.

"Biocompatible" and "biologically compatible", as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "pharmaceutically acceptable", as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier", as used herein, refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The term "small molecule", as used herein, generally refers to an organic molecule that is less than about 2000 g/mol in molecular weight, less than about 1500 g/mol, less than about 1000 g/mol, less than about 800 g/mol, or less than about 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups.

"Hydrophilic," as used herein, refers to the property of having affinity for water. For example, hydrophilic polymers (or hydrophilic polymer segments) are polymers (or polymer segments) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer segment), the more that polymer (or polymer segment) tends to not dissolve in, not mix with, or not be wetted by water.

Hydrophilicity and hydrophobicity can be spoken of in relative terms, such as, but not limited to, a spectrum of hydrophilicity/hydrophobicity within a group of polymers or polymer segments. In some embodiments wherein two or more polymers are being discussed, the term "hydrophobic polymer" can be defined based on the polymer's relative hydrophobicity when compared to another, more hydrophilic polymer.

The term "lipophilic", as used herein, refers to compounds having an affinity for lipids.

The term "amphiphilic", as used herein, refers to a molecule combining hydrophilic and lipophilic (hydrophobic) properties.

"Nanoparticle", as used herein, generally refers to a particle having a diameter, such as an average diameter, from about 10 nm up to but not including about 1 micron, preferably from 100 nm to about 1 micron. The particles can have any shape. Nanoparticles having a spherical shape are generally referred to as "nanospheres".

"Microparticle", as used herein, generally refers to a particle having a diameter, such as an average diameter, from about 1 micron to about 100 microns, preferably from about 1 to about 50 microns, more preferably from about 1 to about 30 microns, most preferably from about 1 micron to about 10 microns. The microparticles can have any shape. Microparticles having a spherical shape are generally referred to as "microspheres".

"Mean particle size" as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution", are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Branch point", as used herein, refers to a portion of a polymer-drug conjugate that serves to connect one or more hydrophilic polymer segments to one or more hydrophobic polymer segments.

The term "targeting moiety", as used herein, refers to a moiety that binds to or localizes to a specific locale. The moiety may be, for example, a protein, nucleic acid, nucleic acid analog, carbohydrate, or small molecule. The locale may be a tissue, a particular cell type, or a subcellular compartment. The targeting moiety or a sufficient plurality of targeting moieties may be used to direct the localization of a particle or an active entity. The active entity may be useful for therapeutic, prophylactic, or diagnostic purposes.

The term "reactive coupling group", as used herein, refers to any chemical functional group capable of reacting with a second functional group to form a covalent bond. The selection of reactive coupling groups is within the ability of the skilled artisan. Examples of reactive coupling groups can include primary amines (—$NH_2$) and amine-reactive linking groups such as isothiocyanates, isocyanates, acyl azides, NHS esters, sulfonyl chlorides, aldehydes, glyoxals, epoxides, oxiranes, carbonates, aryl halides, imidoesters, carbodiimides, anhydrides, and fluorophenyl esters. Most of these conjugate to amines by either acylation or alkylation. Examples of reactive coupling groups can include aldehydes (—COH) and aldehyde reactive linking groups such as hydrazides, alkoxyamines, and primary amines. Examples of reactive coupling groups can include thiol groups (—SH) and sulfhydryl reactive groups such as maleimides, haloacetyls, and pyridyl disulfides. Examples of reactive coupling groups can include photoreactive coupling groups such as aryl azides or diazirines. The coupling reaction may include the use of a catalyst, heat, pH buffers, light, or a combination thereof.

The term "protective group", as used herein, refers to a functional group that can be added to and/or substituted for another desired functional group to protect the desired functional group from certain reaction conditions and selectively removed and/or replaced to deprotect or expose the desired functional group. Protective groups are known to the skilled artisan. Suitable protective groups may include those described in Greene, T. W. and Wuts, P. G. M., Protective Groups in Organic Synthesis, (1991). Acid sensitive protective groups include dimethoxytrityl (DMT), tert-butylcarbamate (tBoc) and trifluoroacetyl (tFA). Base sensitive protective groups include 9-fluorenylmethoxycarbonyl (Fmoc), isobutyrl (iBu), benzoyl (Bz) and phenoxyacetyl (pac). Other protective groups include acetamidomethyl, acetyl, tert-amyloxycarbonyl, benzyl, benzyloxycarbonyl, 2-(4-biphenylyl)-2-propyloxycarbonyl, 2-bromobenzyloxycarbonyl, tert-butyl, tert-butyloxycarbonyl, 1-carbobenzoxamido-2,2,2-trifluoroethyl, 2,6-dichlorobenzyl, 2-(3,5-dimethoxyphenyl)-2-propyloxycarbonyl, 2,4-dinitrophenyl, dithiasuccinyl, formyl, 4-methoxybenzenesulfonyl, 4-methoxybenzyl, 4-methylbenzyl, o-nitrophenylsulfenyl, 2-phenyl-2-propyloxycarbonyl, α-2,4,5-tetramethylbenzyloxycarbonyl, p-toluenesulfonyl, xanthenyl, benzyl ester, N-hydroxysuccinimide ester, p-nitrobenzyl ester, p-nitrophenyl ester, phenyl ester, p-nitrocarbonate, p-nitrobenzylcarbonate, trimethylsilyl and pentachlorophenyl ester.

II. Core-Shell Microparticles and Nanoparticles

A. Core

The core of the particles is formed of or contains one or more hydrophobic materials, typically polymers (e.g., homopolymer, copolymer, terpolymer, etc.). The material may be biodegradable or non-biodegradable. In some embodiments, the one or more materials are one or more biodegradable polymers.

In general, synthetic polymers are preferred, although natural polymers may be used and have equivalent or even better properties, especially some of the natural biopolymers which degrade by hydrolysis, such as some of the polyhydroxyalkanoates. Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. As used herein, "derivatives" include polymers having substitutions, additions of chemical groups and other modifications routinely made by those skilled in the art.

Examples of preferred non-biodegradable polymers include ethylene vinyl acetate, poly(meth)acrylic acid, polyamides, copolymers and mixtures thereof.

In certain embodiments, the hydrophobic polymer is an aliphatic polyester. In preferred embodiments, the hydrophobic polymer is poly(lactic acid), poly(glycolic acid), or poly(lactic acid-co-glycolic acid). The particles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. The hydrophobic poly (lactic acid) (PLA), more hydrophilic poly (glycolic acid) PGA and their copolymers, poly (lactide-co-glycolide) (PLGA) have different release rates. The degradation rate of these polymers, and often the corresponding drug release rate, can vary from days (PGA) to months (PLA) and is easily manipulated by varying the ratio of PLA to PGA. The core can be formed of copolymers including amphiphilic copolymers such as PLGA-PEG or PLURONICS (block copolymers of polyethylene oxide-polypropylene glycol) but this may decrease the benefit of the polyglycerol molecules discussed below.

Other materials may also be incorporated including lipids, fatty acids, and phospholipids. These may be dispersed in or on the particles, or interspersed with the polyglycerol coatings discussed below.

B. Shell

The particles include a shell or coating containing hyperbranched polyglycerol (HPG).

Hyperbranched polyglycerol is a highly branched polyol containing a polyether scaffold. Hyperbranched polyglycerol can be prepared using techniques known in the art. It can be formed from controlled etherification of glycerol via cationic or anionic ring opening multibranching polymerization of glycidol. For example, an initiator having multiple reactive sites is reacted with glycidol in the presence of a base to form hyperbranched polyglycerol (HPG). Suitable initiators include, but are not limited to, polyols, e.g., triols, tetraols, pentaols, or greater and polyamines, e.g., triamines, tetraamines, pentaamines, etc. In one embodiment, the initiator is 1,1,1-trihydroxymethyl propane (THP).

A formula for hyperbranched polyglycerol as described in EP 2754684 is

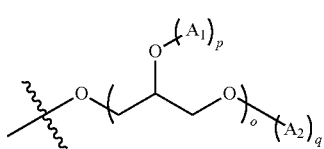

Formula I wherein o, p and q are independently integers from 1-100, wherein $A_1$ and $A_2$ are independently

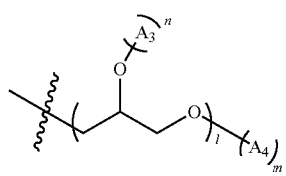

Formula II wherein l, m and n are independently integers from 1-100. wherein $A_3$ and $A_4$ are defined as $A_1$ and $A_2$, with the proviso that $A_3$ and $A_4$ are hydrogen, n and m are each 1 for terminal residues.

The surface properties of the HPG can be adjusted based on the chemistry of vicinal diols. For example, the surface properties can be tuned to provide stealth particles, i.e., particles that are not cleared by the MPS due to the presence of the hydroxyl groups; adhesive (sticky) particles, i.e., particles that adhere to the surface of tissues, for example, due to the presence of one or more reactive functional groups, such as aldehydes, amines, oxime, or O-substituted oxime that can be prepared from the vicinal hydroxyl moieties; or targeting by the introduction of one or more targeting moieties which can be conjugated directly or indirectly to the vicinal hydroxyl moieties. Indirectly refers to transformation of the hydroxy groups to reactive functional groups that can react with functional groups on molecules to be attached to the surface, such as active agents and/or targeting moieties, etc. A schematic of this tunability is shown in FIG. 1A showing bioadhesive polymer.

The hyperbranched nature of the polyglycerol allows for a much higher density of hydroxyl groups, reactive functional groups, and/or targeting moieties than obtained with linear polyethylene glycol. For example, the particles can have a density of surface functionality (e.g., hydroxyl groups, reactive functional groups, and/or targeting moieties) of at least about 1, 2, 3, 4, 5, 6, 7, or 8 groups/nm².

The molecular weight of the HPG can vary. For example, in those embodiments wherein the HPG is covalently attached to the materials or polymers that form the core, the molecular weight can vary depending on the molecular weight and/or hydrophobicity of the core materials. The molecular weight of the HPG is generally from about 1,000 to about 1,000,000 Daltons, from about 1,000 to about 500,000 Daltons, from about 1,000 to about 250,000 Daltons, or from about 1,000 to about 100,000 Daltons. In those embodiments wherein the HPG is covalently bound to the core materials, the weight percent of HPG of the copolymer is from about 1% to about 50%, such as about 1, 2, 3, 4, 5, 10, 15, 20, 25, 30, 35, 40, 45 or 50%.

In some embodiments, the HPG is covalently coupled to a hydrophobic material or a more hydrophobic material, such as a polymer. Upon self-assembly, particles are formed containing a core containing the hydrophobic material and a shell or coating of HPG. HPG coupled to the polymer PLA is shown below:

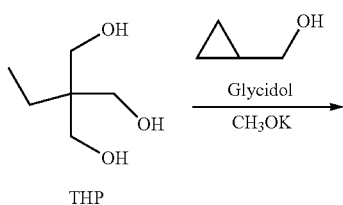

-continued

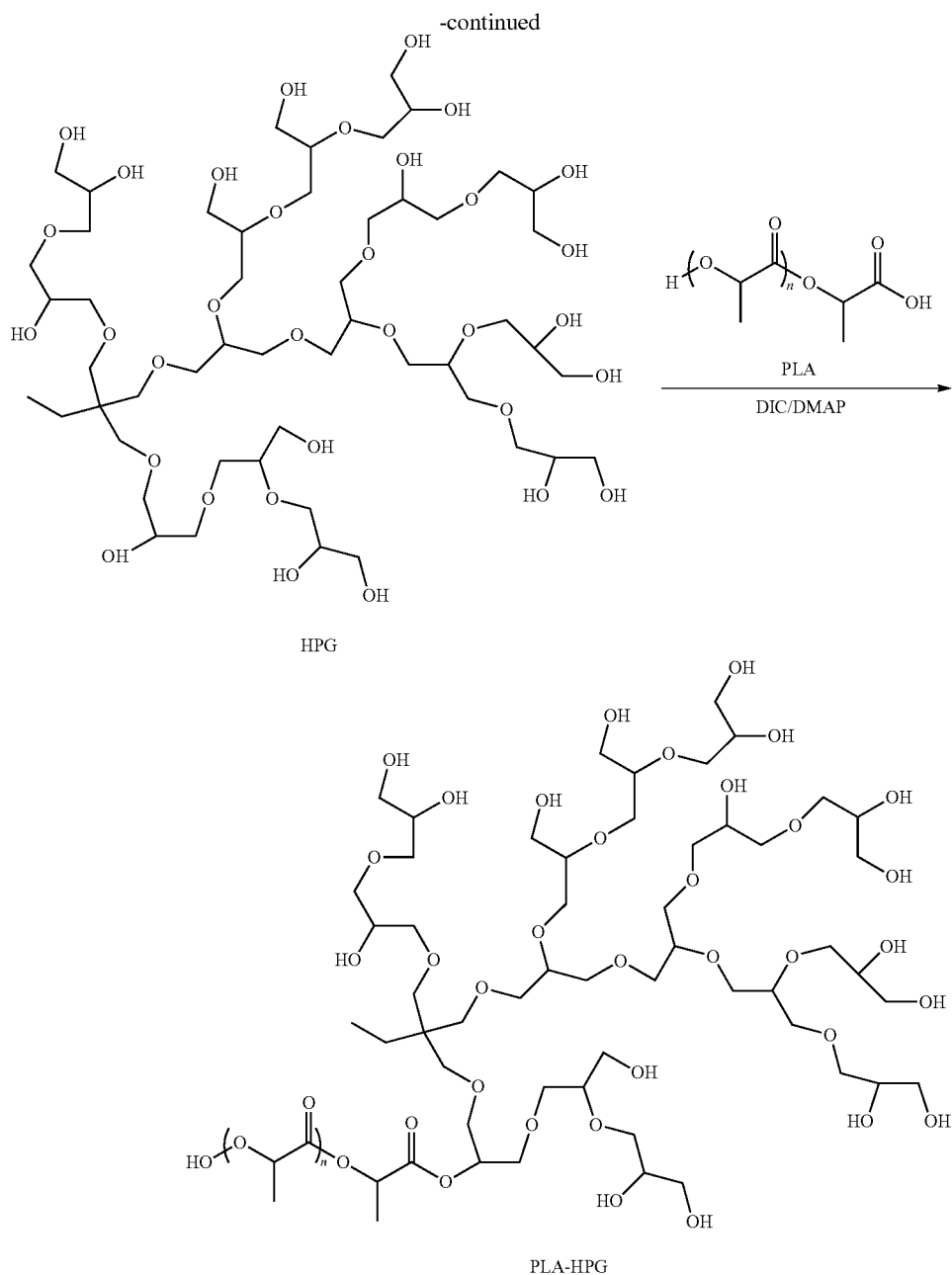

HPG

PLA-HPG

C. Molecules to be Encapsulated or Attached to the Surface of the Particles

The particles may contain one or more types of molecules encapsulated within and/or attached to the surface of the particles. The molecules can be covalently or non-covalently associated with the particles.

In preferred embodiments, the molecules are pigments or particles blocking or filtering ultraviolet ("UV") radiation.

In some embodiments, the molecules are targeting moieties which are covalently associated with the particles. In particular embodiments, the targeting moieties are covalently bound to the HPG coating via the hydroxy groups on HPG. The targeting moieties can be bound directly to HPG or via a coupling agent. In other embodiments, the particles have encapsulated therein one or more therapeutic agents, diagnostic agents, prophylactic agents, and/or nutraceuticals. In some embodiments, the particles contain both targeting agents which are covalently or non-covalently associated with the particles and one or more therapeutic agents, diagnostic agents, prophylactic agents, and/or nutraceuticals which are covalently or non-covalently associated with the particles.

Molecules can be bound to the hydroxy groups on HPG before or after particle formation. Representative methodologies for conjugated molecules to the hydroxy groups on HPG are described below.

One useful protocol involves the "activation" of hydroxyl groups with carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8.

Alternatively, the hydroxyl groups can be converted to reactive functional group that can react with a reactive functional group on the molecule to be attached. For example, the hydroxyl groups on HPG can be converted to aldehydes, amines, or O-substituted oximes which can react with reactive functional groups on molecules to be attached. Such transformations can be done before or after particle formation.

Any suitable coupling method known to those skilled in the art for the coupling of ligands and polymers with double bonds, including the use of UV crosslinking, may be used for attachment of molecules to the polymer.

Coupling is preferably by covalent binding but it may also be indirect, for example, through a linker bound to the polymer or through an interaction between two molecules such as strepavidin and biotin. It may also be by electrostatic attraction by dip-coating.

The coupling methods can be done before or after particle formation.

1. Ultraviolet Light Filters and Pigments

Ultraviolet light filters (such as zinc oxide (ZnO), titanium dioxide (TiO2), avobenzone, tinosorb S, mexoryl SX, mexoryl XL, helioplex, octinoxate, octocrylene, oxybenzone, octisalate, homosalate, uvinul T 150, cinoxate, aminobenzoic acid, padimate O, ensulizole, dioxybenzone, meradimate, sulisobenzone, trolamine salicylate, enzacamene, bisdisulizole disodium, uvinul A Plus, uvasorb HEB, parsol SLX, amiloxate), antibiotics, antiseptics, antifungals, and anesthetic compounds (such as lidocaine, benzocaine, chloroprocaine, cyclomethycaine, dimethocaine/larocaine, piperocaine, propoxycaine, procaine/novocaine, proparacaine, tetracaine/amethocaine, lidocaine, articaine, bupivacaine, cinchocaine/dibucaine, etidocaine, levobupivacaine, lidocaine/lignocaine, mepivacaine, prilocaine, ropivacaine, trimecaine, lidocaine/prilocaine, lidocaine/tetracaine, prilocaine hydrochloride and epinephrine, lidocaine, bupivacaine, and epinephrine, iontocaine, septocaine, saxitoxin, neosaxitoxin, tetrodotoxin, menthol). Prophylactic compounds can also include other components commonly used in lotions, creams and gels, such as fragrances, glycerol, petroleum jelly, dyes, preservatives, proteins, stabilizing agents, ferric oxide ($Fe_2O_3$), zinc carbonate, or mixtures thereof. Prophylactic agents can also include antioxidants. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and sodium sulfite.

Particularly preferred agents to be delivered include UV filters, such as padimate O (PO), zinc oxide (ZnO), titanium dioxide (TiO2), silicon oxide coated ZnO or $TiO_2$, avobenzone, tinosorb S, mexoryl SX, mexoryl XL, helioplex, octinoxate, octocrylene, oxybenzone, octisalate, homosalate, uvinul T 150, cinoxate, aminobenzoic acid, ensulizole, dioxybenzone, meradimate, sulisobenzone, trolamine salicylate, enzacamene, bisdisulizole disodium, uvinul A Plus, uvasorb HEB, parsol SLX, and amiloxate. Incorporated into microparticles, these agents may be used to prevent skin conditions and skin diseases.

2. Active Agents: Therapeutic Agents, Diagnostic Agents, Prophylactic Agents, and/or Nutraceuticals Additional agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered. The preferred materials to be incorporated are prophylactic agents, such as UV filters, anti-oxidants, anesthetics, corticosteroids, anti-acne agents, and vitamins. Other preferred materials to be incorporated are therapeutic agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, SFU, methotrexate, adriamycin, camptothecin, epothilones A-F, and taxol), peptide drugs, anti-inflammatories, and nutraceuticals.

Representative classes of diagnostic materials include paramagnetic molecules, fluorescent compounds, magnetic molecules, and radionuclides. Exemplary materials include, but are not limited to, metal oxides, such as iron oxide, metallic particles, such as gold particles, etc. Biomarkers can also be conjugated to the surface for diagnostic applications.

One or more active agents may be formulated alone or with excipients or encapsulated on, in or incorporated into the microparticles or nanoparticles. Active agents include therapeutic, prophylactic, neutraceutical and diagnostic agents. Any suitable agent may be used. These include organic compounds, inorganic compounds, proteins, polysaccharides, nucleic acids or other materials that can be incorporated using standard techniques.

For imaging, radioactive materials such as Technetium99 ($^{99m}Tc$) or magnetic materials such as $Fe_2O_3$ could be used. Examples of other materials include gases or gas emitting compounds, which are radioopaque.

Alternatively, the biodegradable polymers may encapsulate cellular materials, such as for example, cellular materials to be delivered to antigen presenting cells as described below to induce immunological responses.

Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA-based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

3. Targeting Moieties

The HPG coated particles can be modified to facilitate targeting or adhesion through the attachment of targeting molecules. Exemplary target molecules include proteins, peptides, nucleic acids, lipids, saccharides, or polysaccharides, or small molecules that bind to one or more targets associated with an organ, tissue, cell, or extracellular matrix. For example, a targeting moiety can be a polypeptide, such as an antibody that specifically recognizes a cell marker that is present exclusively or in higher amounts on a target cell (e.g., a keratinocyte cell antigen).

Targeting molecules can be covalently bound to particles using a variety of methods known in the art. In some embodiments, the targeting moieties are covalently associated with the polymer, preferably via a linker cleaved at the site of delivery.

The nanoparticles can contain one or more polymer conjugates containing end-to-end linkages between the polymer and a targeting element or a detectable label. For example, a modified polymer can be a PLA-HPG-peptide block polymer.

Examples of targeting moieties include peptides such as iRGD, LyP1; small molecule such as folate, aptamers and antibodies, such as antibodies to integrins or skin cell receptors, or their combinations at various molar ratios.

The targeting element of the nanoparticle can be an antibody or antigen binding fragment thereof. The targeting elements should have an affinity for a cell-surface receptor or cell-surface antigen on the target cells and result in binding of the particle to the target cell.

The target molecule can be a cell surface polypeptide, lipid, or glycolipid. Cell specific markers can be for specific types of cells including, but not limited to stem cells, skin cells, follicle cells, and infected skin cells. The cell markers can be specific for endothelial, ectodermal, or mesenchymal cells. Representative cell specific markers include, but are not limited to cancer specific markers.

The targeting element can be a peptide. Specifically, the plaque targeted peptide can be, but is not limited to, one or more of the following: RGD, iRGD(CRGDK/RGPD/EC), LyP-1, P3(CKGGRAKDC), or their combinations at various molar ratios. The targeting peptides can be covalently associated with the polymer and the covalent association can be mediated by a linker.

The targeting element can be an antibody or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. The antigen binding portion of the antibody can be any portion that has at least one antigen binding site, such as Fab, F(ab')$_2$, dsFv, sFv, diabodies, and triabodies. In certain embodiments, the antibody is a single chain antibody.

Aptamers are oligonucleotide or peptide sequences with the capacity to recognize virtually any class of target molecules with high affinity and specificity. Aptamers bind to targets such as small organics, peptides, proteins, cells, and tissues. Unlike antibodies, some aptamers exhibit stereoselectivity. The aptamers can be designed to bind to specific targets expressed on cells, tissues or organs.

The outer surface of the particle may be treated using a mannose amine, thereby mannosylating the outer surface of the particle. This treatment may cause the particle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

The attachment of any positively charged ligand, such as polyethyleneimine or polylysine, to any particle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microparticles with the appropriate chemistry. For example, polyclonal antibodies raised against components of mucin or else intact mucin, when covalently coupled to particles, would provide for increased bioadhesion. The ligand affinity need not be based only on electrostatic charge, but other useful physical parameters such as solubility in mucin or else specific affinity to carbohydrate groups.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range would yield chains of 120 to 425 amino acid residues attached to the surface of the particles. The polyamino chains would increase bioadhesion by means of chain entanglement in mucin strands as well as by increased carboxylic charge.

4. Sheddable Polyethylene Glycol (PEG) Coatings

The HPG-coated particles can be modified by covalently attaching PEG to the surface. This can be achieved by converting the vicinyl diol groups to aldehydes and then reacting the aldehydes with functional groups on PEG, such as aliphatic amines, aromatic amines, hydrazines and thiols. The linker has end groups such as aliphatic amines, aromatic amines, hydrazines, thiols and O-substituted oxyamines. The bond inserted in the linker can be disulfide, orthoester and peptides sensitive to proteases.

PEG with a functional group or a linker can form a bond with aldehyde on PLA-HPGALD and reversed the bioadhesive (sticky) state of PLA-HPGALD to stealth state. This bond or the linker is labile to pH change or high concentration of peptides, proteins and other biomolecules. After administration systematically or locally, the bond attaching the PEG to PLA-HPGALD can be reversed or cleaved to release the PEG in response to environment and exposed the PLA-HPGALD particles to the environment. Subsequently, the particles will interact with the tissue and attach the particles to the tissues or extracellular materials such as proteins. The environment can be acidic environment in tumors, reducing environment in tumors, protein rich environment in tissues.

III. Methods of Making Particles and Modification Thereof

A. Methods of Making Polymeric Particles

Methods of making polymeric particles are known in the art. Common microencapsulation techniques include, but are not limited to, spray drying, interfacial polymerization, hot melt encapsulation, phase separation encapsulation (spontaneous emulsion microencapsulation, solvent evaporation microencapsulation, and solvent removal microencapsulation), coacervation, low temperature microsphere formation, and phase inversion nanoencapsulation (PIN). A brief summary of these methods is presented below.

In some embodiments, the particles are prepared using an emulsion-based technique. In particular embodiments, the particles are prepared using a double emulsion solvent evaporation technique. For example, the amphiphilic material and the hydrophobic cationic material are dissolved in a suitable organic solvent, such as methylene chloride or dichloromethane (DCM), with or without agent to be encapsulated.

1. Phase Separation Microencapsulation

In phase separation microencapsulation techniques, a polymer solution is stirred, optionally in the presence of one or more active agents to be encapsulated. While continuing to uniformly suspend the material through stirring, a nonsolvent for the polymer is slowly added to the solution to decrease the polymer's solubility. Depending on the solubility of the polymer in the solvent and nonsolvent, the polymer either precipitates or phase separates into a polymer rich and a polymer poor phase. Under proper conditions, the polymer in the polymer rich phase will migrate to the interface with the continuous phase, encapsulating the active agent(s) in a droplet with an outer polymer shell.

2. Spontaneous Emulsion Microencapsulation

Spontaneous emulsification involves solidifying emulsified liquid polymer droplets formed above by changing temperature, evaporating solvent, or adding chemical cross-linking agents. The physical and chemical properties of the encapsulant, as well as the properties of the one or more active agents optionally incorporated into the nascent particles, dictates suitable methods of encapsulation. Factors such as hydrophobicity, molecular weight, chemical stability, and thermal stability affect encapsulation.

3. Solvent Evaporation Microencapsulation Methods for forming microspheres using solvent evaporation techniques are described in E. Mathiowitz et al., *J. Scanning Microscopy*, 4:329 (1990); L. R. Beck et al., *Feral. Steril.*, 31:545 (1979); L. R. Beck et al, *Am. J Obstet. Gynecol.*, 135(3) (1979); S. Benita et al., *J Pharm. Sci.*, 73:1721 (1984); and U.S. Pat. No. 3,960,757 to Morishita et al. The polymer is dissolved in a volatile organic solvent, such as methylene chloride. One or more active agents to be incorporated are optionally added to the solution, and the mixture is suspended in an aqueous solution that contains a surface active agent such as poly(vinyl alcohol). The resulting emulsion is stirred until most of the organic solvent evaporated, leaving solid microparticles/nanoparticles. This method is useful for relatively stable polymers like polyesters and polystyrene.

4. Phase Inversion Nanoencapsulation (PIN)

Nanoparticles can also be formed using the phase inversion nanoencapsulation (PIN) method, wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. See, e.g., U.S. Pat. No. 6,143,211 to Mathiowitz, et al. The method can be used to produce monodisperse populations of nanoparticles and microparticles in a wide range of sizes, including, for example, about 100 nanometers to about 10 microns.

5. Microfluidics

Nanoparticles can be prepared using microfluidic devices. A polymeric material is mixed with a drug or drug combinations in a water miscible organic solvent. The water miscible organic solvent can be one or more of the following: acetone, ethanol, methanol, isopropyl alcohol, acetonitrile and Dimethyl sulfoxide (DMSO). The resulting mixture solution is then added to an aqueous solution to yield nanoparticle solution.

B. HPG Conjugates or Coatings

Hyperbranched polyglycerol (HPG) can be covalently bound to one or more materials, such as a polymer, that form the core of the particles using methodologies known in the art. For example, HPG can be covalently coupled to a polymer having carboxylic acid groups, such as PLA, PGA, or PLGA using DIC/DMAP. In another example, the HPG can be initiated from special functionalized initiators to facilitate the conjugation to more materials. These special initiators include disulfide (Yeh et al., *Langmuir*. 24(9): 4907-16 (2008)).

Figure 1B:
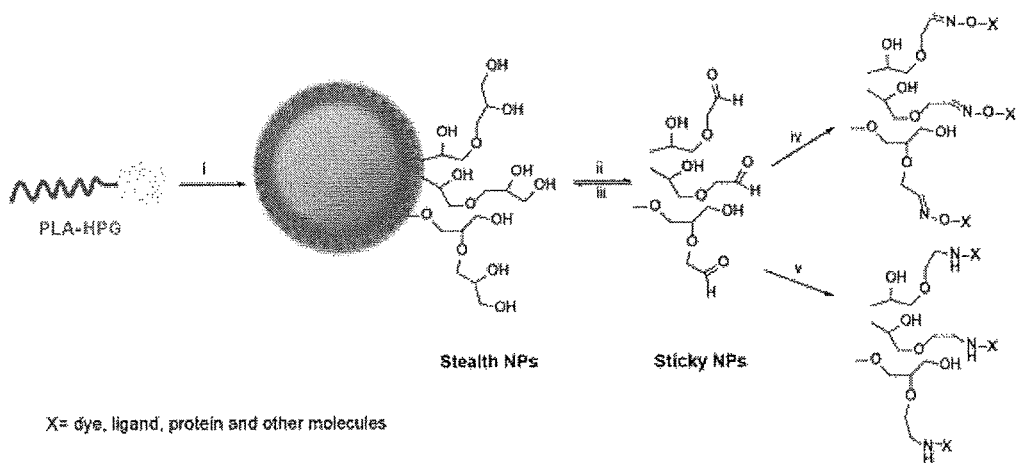
FIG. 1B is a schematic showing the synthesis of stealth nanoparticles and sticky nanoparticles.

The HPG can be functionalized to introduce one or more reactive functional groups that alter the surface properties of the particles. For example, HPG-coated particles prevent non-specific adsorption of serum proteins and increase the blood circulation of the particles. Such particles are referred to as stealth particle. However, the hydroxyl groups on HPG can be chemically modified to cause the particles to stick to biological material, such as tissues, organs, cells, etc. Such functional groups include aldehydes, amines, O-substituted oximes, and combinations thereof. A synthetic scheme for such chemical conversions is shown in FIG. 1.

The surface of the particles can further be modified with one or more targeting moieties or covalently bound to HPG via a coupling agent or spacer in organic solvents such as dichloromethane (DCM), dimethylformamide (DMF), dimethyl sulfoxide (DMSO) or tetrahydrofuran (THF). In some embodiments, the polymer is functionalized/modified before nanoparticle formation. Alternatively, the targeting moieties may be attached to NPs after the synthesis of NPs in aqueous solution (or other protic solution such as alcohol). For example, HPG coated NPs can be transformed to aldehyde terminated NPs by $NaIO_4$ treatment (or carboxylic acid terminated by $NaIO_4$ treatment followed by sodium chlorite treatment) so the targeting moieties may be directly covalently attached to NPs via aldehyde (or carboxylic acid) groups on NPs and functional groups (amine, hydrazine, aminooxy and their derivatives) on the targeting moieties or indirectly attached to the NPs via coupling agents or spacers (such as aminooxy modified biotin and cysteine).

Certain properties of the PLA-HPG conjugate are important for the observed effects. Because high molecular weight HPG has better resistance of non-specific adsorption to biomolecules, the low molecular weight components are removed from the synthesized HPG by multiple solvent precipitations and dialysis.

In the preferred embodiment, a polyhydroxy acid such as PLA is selected as the hydrophobic core material because it is biodegradable, has a long history of clinical use, and is the major component of a NP system that is advancing in clinical trials. To covalently attach the PLA to HPG, the previous approach was to first functionalize the HPG with an amine and then conjugate the carboxylic group on PLA to the amine. This approach is efficient but cannot be used to make HPG as surface coatings since any amines that do not react with PLA will lead to a net positive charge on the neutral HPG surface and reduce the ability of HPG to resist adsorption of other molecules on the surface. To avoid this, the approach in the examples uses a one-step esterification between PLA and HPG, which maintained the charge neutral state of the HPG.

Targeting molecules or agents to be encapsulated or delivered may be associated with the surface of, encapsulated within, surrounded by, and/or distributed throughout the polymeric matrix of the particles.

C. Particle Properties

The particles may have any zeta potential. The particles can have a zeta potential from −300 mV to +300 mV, −100 mV to +100 mV, from −50 mV to +50 mV, from −40 mV to +40 mV, from −30 mV to +30 mV, from −20 mV to +20 mV, from −10 mV to +10 mV, or from −5 mV to +5 mV. The particles can have a negative or positive zeta potential. In some embodiments the particles have a substantially neutral zeta potential, i.e. the zeta potential is approximately 0 mV. In preferred embodiments the particles have a zeta potential of approximately −30 to about 30 mV, preferably from about −20 to about 20 mV, more preferably from about −10 to about 10 mV.

The particles may have any diameter. The particles can have a diameter of about 1 nm to about 1000 microns, about 1 nm to about 100 microns, about 1 nm to about 10 microns, about 1 nm to about 1000 nm, about 1 nm to about 500 nm, about 1 nm to about 250 nm, or about 1 nm to about 100 nm. In preferred embodiments, the particle is a nanoparticle having a diameter from about 25 nm to about 250 nm. In more preferred embodiments, the particles are nanoparticles having a diameter from about 180 nm to about 250 nm, preferably from about 180 nm to about 230 nm.

The polydispersity is from about 0.05 to 0.30, preferably from about 0.05 to about 0.25, more preferably from about 0.05 to about 0.20, more preferably from about 0.05 to about 0.15, most preferably from about 0.05 to about 0.10.

IV. Topical and Pharmaceutical Formulations

The particles can be formulated with appropriate pharmaceutically acceptable carriers into pharmaceutical compositions for administration to an individual in need thereof. The formulations can be administered topically (e.g., to the skin via non-invasive topical application). Other routes of administration include, but are not limited to, transdermal.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, viscosity modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, benzalkonium, sorbic acid, and thimerosal. The formulation may also contain an antioxidant to prevent degradation of the active agent(s).

The formulation is typically buffered to a pH of 3-8. Suitable buffers include, but are not limited to, phosphate buffers, acetate buffers, and citrate buffers.

Water soluble polymers may be used in formulations. Suitable water-soluble polymers include, but are not limited to, polyvinylpyrrolidone, dextran, carboxymethylcellulose, and polyethylene glycol.

Carrier also includes all components of the coating composition which may include plasticizers, pigments, colorants, stabilizing agents, and glidants. Formulations can be prepared using one or more topical or pharmaceutically acceptable excipients, including diluents, preservatives, binders, lubricants, disintegrators, swelling agents, fillers, stabilizers, and combinations thereof.

Stabilizers are used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

V. Methods of Using Particles

The particles can be used for a variety of applications including protecting tissue from from UV light, drug delivery, tissue engineering, etc. In some embodiments, the particles are "stealth" particles, where the hydroxyl groups on HPG resist non-specific protein absorption. This can allow targeted particles to be delivered to the desired site for drug release. Such stealth properties can also be useful for topical delivery, for example, diffusion into hair follicles to release agents to promote hair growth/prevent hair loss or agents that promote hair loss. Alternatively, the vicinyl diol groups can be converted to functional groups that adhere to biological materials, such as tissue (e.g., cornea), organs (e.g., skin), cells, proteins, etc. Such particles are referred to as "sticky".

The particles can be used to deliver one or more therapeutic agents, diagnostic agents, prophylactic agents, nutraceuticals, or combinations thereof to the skin. As discussed above, the vicinyl diol groups on HPG can be chemically transformed to functional groups that make the particle adhere or stick to tissue or other biological materials, such as skin (e.g., sticky particles). Incubation of HPG-coated particles with the reagent $NaIO_4$, which converts vicinyl diol groups to aldehyde groups, showed an estimated 8 aldehyde groups/nm$^2$ after about 20 minutes. Surface immobilization of HPG particles on lysine-coated slides increased as the incubation time with $NaIO_4$ increased.

Aldehyde-functionalized HPG-coated particles loaded with the dye DiD were incubated with pig skin for 6 hours. The relative fluorescence of the aldehyde-functionalized particles was three-fold higher than the relative fluorescence of HPG-coated particles.

In view of the data above, the particles can be used for delivery of one or more active agents to the skin. In some embodiments, the particles can be used as or formulated in a sunscreen. For example, the particles were loaded with padimate O (PO), an organic compound used in suncreens. Under conditions mimicking the pH range of human sweat (4.5 and 7.4), the particles retained more than about 96% of the PO after 20 hours. The particles also exhibited improved UV absorption compared to PO dispersed in water or aqueous buffer.

Other agents include agents for treating skin aging, such as anti-reactive oxygen species (ROS) therapies.

The particles can also be used to deliver agents to hair follicles, for examples, agents to promote hair growth or reduce hair loss or therapies to remove hair. The stealth nature of the particles can allow diffusion of the particles into the hair follicles.

A chronic wound is a wound that does not heal normally. Wounds that do not heal within three months are often considered chronic. One embodiment provides administering an effective amount of the particles to a chronic wound to promote or enhance healing.

The disclosed particles can also be used to treat fibrotic wounds. Fibrotic wounds have dysregulated healing and typically delayed healing. Fibrosis can be defined as the replacement of the normal structural elements of the tissue by distorted, non-functional and excessive accumulation of scar tissue. One embodiment provides a method for treating fibrotic wounds by administering an effective amount of the disclosed particles to promote or enhance fibrotic wound healing.

The particles can also be used with wound dressings. One embodiment provides a wound dressing having a layer of particles on the wound dressing. The layer of particles is configured to come into contact with the wound when the wound dressing is applied to a wound. The particles can be impregnated in the wound dressing or coated on the wound dressing using conventional techniques. The wound dressing can be made of absorbent materials such as cotton or fleece. The wound dressing can also be made of synthetic fibers, for example, polyamide fibers. In certain embodiments, the wound dressing can have multiple layers including an adhesive layer, an absorbent layer, and moisture regulation layer. The wound dressing can also include antimicrobial agents, antifungal agents, and other active agents to promote wound healing such as cytokines and growth factors discussed above.

Another embodiment provides a method for treating a wound by administering an effective amount of the disclosed particles to the wound to promote or induce hemostasis and then applying a wound dressing to the wound.

The advantage of these particles is that they adhere to the skin and/or applied material, where they are retained at the site of injury to provide sustained treatment. Mixtures releasing different amounts or different drugs at different times are particularly advantageous for treatment of wounds such as diabetic wound ulcers. Ligands can be selected to enhance the particles being retained at the site, by binding to extracellular matrix or through non-specific electrostatic binding.

The present invention will be further understood in view of the following non-limiting examples.

EXAMPLES

Example 1: Preparation of HPG Coated Particles

Materials and Methods

Polylactic acid (Mw=20.2 kDa, Mn=12.4 kDa) was obtained from Lactel.

$H_2N$-PEG(5000)-$OCH_3$ was obtained from Laysan.

Anhydrous dimethylformide, dichloromethane, diisopropylcarboimide, dimethylaminopyridie, potassium methoxide, camptothecin, polyvinyl alcohol, paraformaldehyde, TWEEN® 80, and 1,1,1-trihydroxymethyl propane were obtained from the Sigma-Aldrich.

Anhydrous dry ether, methanol, acetonitrile and dimethylsulfoxide were obtained from J. T. Baker.

1,1'-Dioctadecyl-3,3,3',3'-Tetramethylindodicarbocyanine, 4 Chlorobenzenesulfonate Salt (DiD) was obtained from Invitrogen.

Super frost microscope slides were obtained from Thermo Scientific.

Microdialysis tubing was from Thermo Scientific.

IR-780 iodide, hydroxylamine solution (50%), glycerol, polyvinyl alcohol, NaIO4 and bovine serum albumin (BSA) were obtained from the Sigma-Aldrich.

The 1,1'-Dioctadecyl-3,3,3',3'-Tetramethylindodicarbocyanine, 4 Chlorobenzenesulfonate Salt (DiD) and DAPI stain were ordered from Invitrogen.

Donkey normal serum and Rabbit-anti-CD31 antibody was provided by Abcam and the Donkey-anti-rabbit secondary antibody tagged with Alexa488 fluorophore was from Invitrogen.

Aldehyde Quantification Assay Kit (Fluorometric) and were from Abcam.

Sunscreen lotion (SPF 30) was purchased from Walgreens.

Sunscreen oil (SPF 30) was from L'Oreal Paris.

Synthesis of Hyperbranched Polyglycerol

Hyperbranched polyglycerol (HPG) was synthesized by anionic polymerization. Briefly, 4.6 mmol 1,1,1-trihydroxypropane (THP) was added into an argon protected flask in a 95° C. oil bath and 1.5 mmol $KOCH_3$ was added. The system was hooked up to a vacuum pump and left under vacuum for 30 min. The system was refilled with argon and 25 ml glycidol was added by a syringe pump over 12 hours. The HPG was dissolved in methanol and precipitated by addition of acetone. HPG was purified 2-3 times with methanol/acetone precipitation. To further remove the low molecular weight HPG, 2-5 ml HPG was placed in a 10 ml dialysis tube (0.5-1 k cut-off) and dialyzed against deionized (DI) water. The water was replaced two times every 12 hours. HPG was precipitated with acetone and then dried under vacuum at 80° C. for 12 h.

Synthesis of PLA-HPG and PLA-PEG Copolymers

PLA (5 g) and 2.15 g HPG were dissolved in dimethyl formamide (DMF) and dried over molecular sieves overnight. 0.06 ml diisopropylcarboimide (DIC) and 10 mg 4-(N,N-dimethylamino)pyridine (DMAP) were added and the reaction proceeded for 5 days at room temperature under stirring. The product was precipitated by pouring the reaction into cold diethyl ether (ether) and collecting the precipitate by centrifugation. The product was redissolved in dichloromethane (DCM) and precipitated again with a cold mixture of ether and methanol. The product was washed with a cold mixture of ether and methanol. The polymer was dried under vacuum for 2 days.

To synthesize PLA-PEG, 2.6 g PLA and 1.0 g MPEG-NH$_2$ were dissolved in DMF and dried over molecular sieves overnight. 0.038 ml DIC was added and the reaction proceeded for 2 days at room temperature under stirring. The product was precipitated by pouring the reaction into cold ether and collecting the precipitate by centrifugation. The product was redissolved in DCM and precipitated again with cold ether, washed with a cold mixture of ether and methanol and dried under vacuum for 2 days.

Fabrication of Nanoparticles (NPs)

Fifty mg of PLA-HPG copolymer dissolved in 1.5-3.0 ml of ethyl acetate/dimethyl sulfoxide (DMSO) (4:1) was added to 4 ml DI water under vortexing and subjected to probe sonication for 3 cycles at 10 sec each. The resulting emulsion was diluted in 20 ml DI water under stirring. It was stirred for at least 5 hours or attached to a ratovapor to evaporate the ethyl acetate and then applied to an Amico ultra centrifuge filtration unit (100 k cut-off). The NPs were washed by filtration 2 times then suspended in a 10% sucrose solution. The NPs were kept frozen at −20° C.

The PLA-PEG NPs were made using a single emulsion technique. 50 mg PLA-PEG copolymer dissolved in 1.5-3.0 ml ethyl acetate/DMSO (4:1) was added to 4 ml DI water with 2.5% PVA under vortexing and subjected to probe sonication for 3 cycles of 10 sec each. The resulting emulsion was diluted in 20 ml DI water with 0.1% Tween® 80 with stirring. The emulsion was stirred for at least 5 hours or attached to a ratovapor to evaporate the ethyl acetate and then the solution was applied to an Amico ultra centrifuge filtration unit (100 k cut-off). The NPs were washed by filtration for 2 times then suspended in a 10% sucrose solution.

Characterization of Nanoparticles (NPs) by Transmission Electron Microscopy (TEM).

The NPs were characterized with TEM. A drop of nanoparticle suspension was applied on the top of carbon coated copper grids and most of the droplet was removed with a piece of filter paper. The thin layer of NPs suspension was dried for 5-10 min and then a droplet of uranyl acetate was applied. Most of the droplet was removed with a filter paper and left to dry for 5 min. The sample was mounted for imaging with TEM. The size distribution of NPs was analyzed in Image J. The hydrodynamic size of NPs was determined by dynamic laser scattering (DLS). NPs suspension was diluted with DI water to 0.05 mg/ml and 1 ml was loaded into the cell for detection.

To determine the concentration of the dye in NPs, 990 µL DMSO was added to 10 µL NPs in aqueous solution. The solution was vortexed and left in the dark for 10 min. The concentration of the dye was quantified with a plate reader by fluorescence of the DiD dye at 670 nm with an excitation wavelength at 644 nm.

Results $^1$H NMR spectra for HPG and PLA-HPG block-copolymer were recorded on a 400 MHz Agilent instrument using DMSO-d6 as solvent. Inverse gated $^{13}$C NMR spectra for HPG were recorded on a 600 MHz Agilent instrument with methanol-d4 as solvent.

The $\overline{DP_n}$ (number-average degree of polymerization) for HPG was calculated according to the inverse gated $^{13}$C NMR spectra for HPG with the following equation:

$$\overline{DP_n} = \frac{(T + L_{13} + L_{14} + D)}{(T - D)} f_c$$

The functionality of the core molecule (TMP), $f_c$, is 3.
The Mn of HPG is calculated with the following equation:

$Mn$=Molecular weight of glycidol×$\overline{DP_n}$ of HPG+ molecular weight of TMP Both particles have a biodegradable PLA core, which can be used to load hydrophobic agents, and a hydrophilic shell of HPG or PEG. HPG was made by anionic polymerization and characterized by $^1$H NMR and $^{13}$C NMR. PLA-HPG copolymer was synthesized by esterification and the conjugation of PLA-HPG was confirmed by $^1$H NMR. The weight percentage of HPG in PLA-HPG was about 29% as calculated from the NMR results.

PLA-HPG NPs were made from a single emulsion as described above. PLA-PEG copolymer was synthesized by the conjugation of PLA-COOH with amine terminated mPEG and also characterized with $^1$H NMR. The weight percentage of PEG was about 26% as calculated from the NMR results.

Transmission electronic microscopy (TEM) confirmed the spherical shape of the PLA-HPG and PLA-PEG NPs. The hydrodynamic diameter of NPs was 100 nm as measured by dynamic light scattering (DLS) (Table 1).

TABLE 1

Average diameter of PLA-HPG nanoparticles and PLA-PEG nanoparticles.

| NPs | Diameter (nm) |
| --- | --- |
| PLA-HPG | 102.1 ± 3.1 |
| PLA-PEG | 103.3 ± 1.0 |

Example 2. Evaluation of NPs In Vitro

Materials and Methods

Microdialysis tubes were filled with 100 µL of NPs loaded with 1,1'-dioctadecyl-3,3,3',3'-tetramethylindodicarbocyanine, 4-chlorobenzenesulfonate Salt (DiD) and placed on a floater in a large beaker with 4 L PBS at 37° C. Tubes were removed in triplicates at different time points. The PBS was changed every 12 hours. The dye left in the dialysis tube was quantified by fluorescence.

Results

Figure 2:
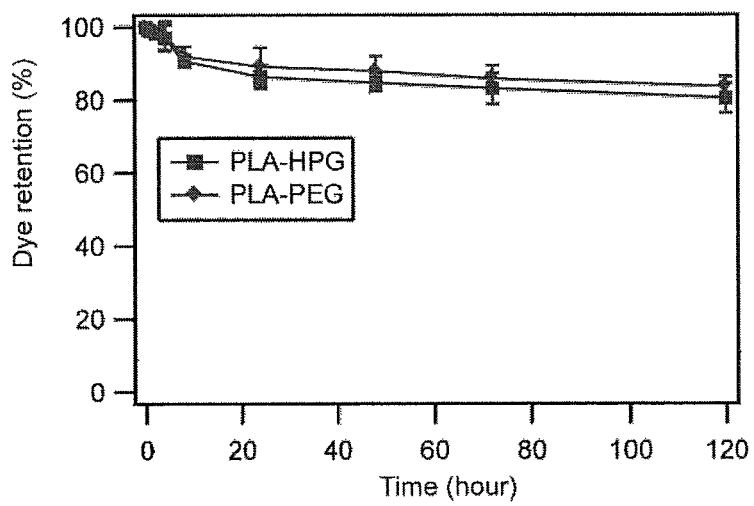
FIG. 2 is a graph showing dye retention (%) of PLA-HPG and PLA-PEG nanoparticles as a function of incubation time in PBS.

DiD-loaded NPs release a minimal amount of dye (~20%) over 5 days of continuous incubation in PBS (FIG. 2). Both PLA-HPG and PLA-PEG NPs were loaded with equivalent amounts of DiD.

Example 3. Evaluation of Reversibility of Stealth Properties of Nanoparticles in Blood Circulation Materials and Methods Synthesis of Functionalized HPG-Coated Nanoparticles.

PLA-HPG NPs (0.1 mg/ml) in a 96-well plate (small vial) were incubated with 1 mM $NaIO_4$ and at each time point, the reactions were quenched with 2 mM $Na_2SO_3$. The NPs were washed two times with DI water in an AcroPrep filter plate with 100 k cut-off (or amicon ultra filter 0.5 ml with 100 k cut-off) and then suspended in DI water.

The aldehydes on NPs were quantified with an aldehyde quantification assay kit (Abcam). The PLA-HPG NPs were used as a background subtraction control. The amount of aldehyde was calculated by comparing to a reference curve. The reference curve was made by using the aldehyde standard provided with the kit. The amount of aldehyde on each particle was calculated based on 100 nm hydrodynamic diameter of NPs and an assumed NP density of 1.0 $g/cm^3$. For microarray printing, NPs load with DiD dye were suspended in PBS buffer containing 15% glycerol and 0.01% triton-X100 at a concentration of 1 mg/ml in a 384-well plate. The NPs were arrayed on lysine coated slides using a Spotbot microrrayer from Arrayit. After 1 hour incubation in a humidity chamber, the printed slides were washed extensively with PBS 3 times, 5 min each. After a quick rinse with DI water, the slides were blow-dried with argon and subjected for imaging.

For ligand or protein attachment, in a 96-well plate (or small vials), PLA-$HPG_{ALD}$ NPs were incubated with ligands or proteins ($NaCNBH_4$ should be added for proteins or ligands modified with amines or hydrazines) for 1 min-12 hours and the reaction was quenched with an excess amount of hydroxylamine (or ethanolamine for proteins or ligands modified with amines or hydrazines) solution in TRIS buffer (PH=7.4). The NPs were transferred to an AcroPrep filter plate with 100 k cut-off (or amicon ultra filter 0.5 ml with 100 k cut-off or gel filtration for proteins and other large molecules) and washed two times with DI water or buffer.

Modification of HPG Surface Properties

To reduce the PLA-$HPG_{ALD}$ NPs (sticky, also referred to herein as bioadhesive nanoparticles, BNPs) back to PLA-HPG NPs (also referred to herein as non-bioadhesive nanoparticles, NNPs), PLA-$HPG_{ALD}$ NPs were incubated with $NaBH_4$ in $NaH_2PO_4$ (0.2M, PH=8.0) and the reaction was quenched with acetic acid and neutralized with PBS buffer. The NPs were washed with DI water twice. The blood circulation experiments were performed to test the stealth properties of the nanoparticles.

Results

PLA-$HPG_{ALD}$ NPs (BNPs) could be reversed to PLA-$HPG_{Reversed}$ (stealth) NPs by $NaBH_4$ treatment, though one alcohol group is lost with the reduction-reversal cycle since each vicinal diol on HPG is oxidized by $NaIO_4$ to an aldehyde and each aldehyde is reduced to a single alcohol by $NaBH_4$. The blood circulation confirmed that the PLA-$HPG_{ALD}$ NPs lost almost all their stickiness after treatment with $NaBH_4$. The back and forth tunability also demonstrated the robustness of the HPG coating on the nanoparticles.

Example 4. Evaluation of Adherence of Functionalized NPs

Materials and Methods

Polylysine coated glass slides were used as a tissue mimic to evaluate the bioadhesive property of PLA-$HPG_{ALD}$ NPs (BNPs). PLA-$HPG_{ALD}$ NPs with different concentrations of aldehydes were prepared using a high-throughput procedure, where regular 96-well plates and 96-well filter plates were used to prepare the NPs and printed onto polylysine coated slides with a microarrayer. The PLA-HPG NPs (NNPs) without $NaIO_4$ treatment did not adhere to glass slides and only background signal was detected. However, by transforming the surface property with $NaIO_4$, the amount of NPs immobilized on the glass slide increased as a function of duration of $NaIO_4$ treatment, indicating that the bioadhesive property of the PLA-HPG NPs can be tuned by control of $NaIO_4$ treatment.

For microarray printing, NPs load with DiD dye were suspended in PBS buffer containing 15% glycerol and 0.01% TRITON®-X100 at a concentration of 1 mg/ml in a 384-well plate. The NPs were arrayed on lysine coated slides using a SPOTBOT® microrrayer from ARRAYIT®. After 1 hour incubation in a humidity chamber, the printed slides were washed extensively with PBS 3 times, 5 min each. After a quick rinse with DI water, the slides were blow-dried with argon and subjected for imaging.

The bioadhesive property of PLA-HPG NPs on tissues was evaluated by applying suspended NPs ex vivo to the external surface of pig skin. Fresh pig skin was obtained from a local slaughterhouse and the hair was carefully removed by a trimmer, making sure no damage occurred to the skin. The skin was frozen at −20° C. The skin was thawed on ice before use. Thawed pig skin was washed with PBS buffer and cut to 2×2 cm pieces. DiD-loaded PLA-HPG NPs (NNPs) and PLA-$HPG_{ALD}$ NPs (BNPs) in PBS were topically applied to pig skin and incubated for 6 h in a humidity chamber at 32° C. After incubation, skin was washed with plenty of PBS buffer and frozen in OCT. The frozen skin was sectioned into 10-20 μm slices, mounted on glass slides, and imaged with an EVOS fluorescence microscope.

For the live imaging study of adherence of PLA-$HPG_{ALD}$ NPs to the skin on Nude mice, the dorsal skin of each Nude mouse was cleaned with an alcohol pad and 1 mg/ml of IR-780/PLA-$HPG_{ALD}$ NPs (0.5%) in PBS was applied to the skin. The nanoparticles remaining on the skin were imaged by XENOGEN®. The mice were housed individually and imaged at each time point. For evaluation of PLA-$HPG_{ALD}$ NPs water resistance and mechanical removal, one group of Nude mice (n=3) was wiped with a wet towel and the other group of mice was washed with water. The mice were subsequently dried with kimwipes and sent for live imaging.

Results

Figure 3A:
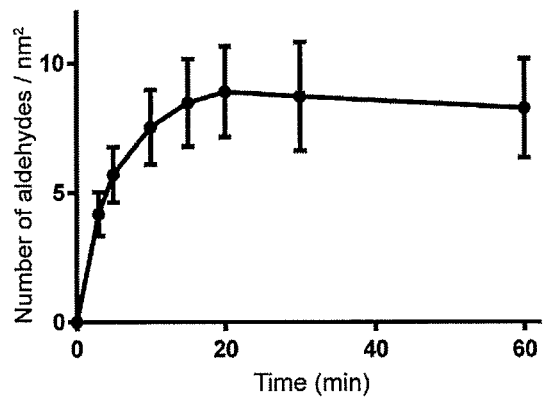
FIG. 3A is a graph showing the number of aldehyde groups/nm$^2$ on stealth NPs as a function of incubation time with NaIO$_4$. Data are shown as mean±SD (n=4).
Figure 3B:
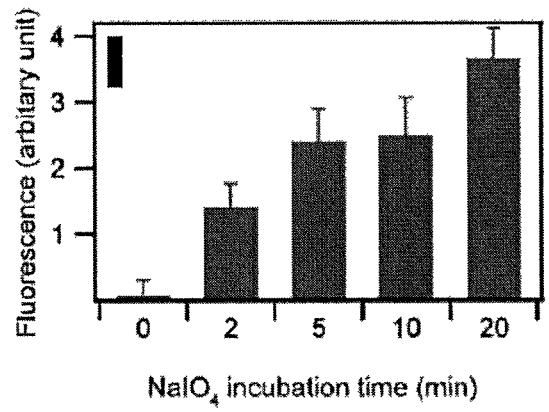
FIG. 3B is a graph showing surface immobilization of DiD loaded PLA-HPG NPs treated with NaIO$_4$ for different periods of time (min) on lysine coated slides. Data are shown as mean±SD (n=4).
Figure 3C:
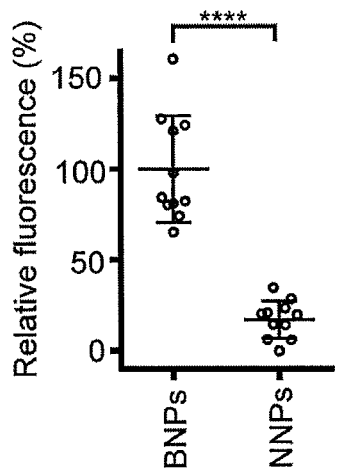
FIG. 3C is a graph of relative fluorescence (%) obtained from sections of pig skin incubated with DiD-loaded PLA-HPG$_{ALD}$ NPs (bioadhesive nanoparticles, BNPs) and DiD-loaded PLA-HPG NPs (non-bioadhesive nanoparticles, NNPs) at 1 mg/ml for 6 hours in a humidity chamber at 32° C. The fluorescence was quantified and normalized to the average fluorescence of the PLA-HPG$_{ALD}$ on pig skin. Data are shown as mean±SD (n=10).

The results are shown in FIGS. 3A-3C. PLA-$HPG_{ALD}$ NPs showed greater retention on pig skin than PLA-HPG NPs (P<0.05). The fluorescence intensity was quantified from the fluorescence images.

Because the HPG coating is rich in vicinal diols, PLA-HPG NPs can be readily oxidized to aldehyde-terminated PLA-$HPG_{ALD}$ NPs by sodium periodate (NaIO4) treatment. This was validated by $H^1NMR$ and Schiffs agent analysis. The surface density of aldehydes on PLA-$HPG_{ALD}$ NPs was monitored as a function of incubation time with $NaIO_4$ and it reached its saturation at about 20 min (FIG. 3A). The final surface density of aldehydes on PLA-$HPG_{ALD}$ NPs approached 9/$nm^2$ (17 aldehydes/PLA molecule), indicating that the majority of surface vicinal diols were converted to aldehydes. This surface density of functional groups is at least one order of magnitude higher than previously reported on biodegradable NPs (Gu et al., *Proc. Natl. Acad. Sci. U.S.A.* 105:2586-2591 (2008)). Moreover, the surface density of the aldehydes can be controlled by incubation time with NaIO$_4$. No detrimental effects of aldehyde conversion were observed on NPs by TEM imaging. The average diameter of NPs was approximately 96 nm by dynamic light scattering (DLS) measurement (Table 2).

The bioadhesive properties of the PLA-HPG$_{ALD}$ NPs (BNPs) using polylysine coated glass slides as a tissue mimic (Rao et al., *J. Biomater. Sci. Polym. Ed.* 22:611-625 (2011)) was investigated. PLA-HPG$_{ALD}$ NPs (BNPs) with different concentrations of aldehyde were prepared and printed onto polylysine coated slides with a microarrayer. PLA-HPG NPs (NNPs) did not adhere to glass slides (FIG. 3B). However, after oxidizing surface HPG vicinal diols into aldehydes with NaIO$_4$, the amount of PLA-HPG$_{ALD}$ NPs immobilized on the glass slide increased as a function of NaIO$_4$ treatment duration (FIG. 3B), indicating that the bioadhesive property of the PLA-HPG$_{ALD}$ NPs increases with a longer duration of NaIO$_4$ treatment. Moreover, the large capacity for surface aldehyde modification allows for tuning adhesiveness for specific topical applications.

TABLE 2

Diameter (nm) and polydispersity index (PDI) of various nanoparticles.

| Nanoparticles (NPs) | Diameter (nm) | PDI |
|---|---|---|
| PLA-HPG$_{ALD}$ | 96 | 0.273 |
| DiD/PLA-HPG | 120 | 0.211 |
| DiD/PLA-HPG$_{ALD}$ | 118 | 0.232 |
| IR-780/PLA-HPG$_{ALD}$ | 128 | 0.334 |
| PO/PLA-HPG$_{ALD}$ | 138 | 0.227 |

Delivery vehicles for UV-filters should ideally remain only on the skin surface, without penetration into the epidermis, dermis, or hair follicles, in order to avoid potential health risks (Krause, et al., *Int. J. Androl.* 35:424-436 (2012)). Thus, the retention and the penetration of PLA-HPG$_{ALD}$ NPs ex vivo to PLA-HPG NPs by applying suspended particles topically onto pig skin was compared. To facilitate imaging and quantification, both NPs were loaded with a hydrophobic dye, 0.2%1,1'-dioctadecyl-3,3,3',3'-tetramethylindodicarbocyanine, 4-chlorobenzenesulfonate salt (DiD) (Deng et al., *Biomaterials.* 35:6595-6602 (2014)). Both the DiD/PLA-HPG NPs and DiD/PLA-HPG$_{ALD}$ NPs were characterized by TEM and DLS (Table 2), and had a similar spherical morphology. After incubation for 6 hours with both NPs, followed by extensive washing, PLA-HPG$_{ALD}$ NPs showed substantially higher retention on pig skin compared to NNPs (FIG. 3C). No penetration of PLA-HPG$_{ALD}$ NPs was observed on any pig skin samples; however, PLA-HPG NPs penetrated into the pig skin follicles without significant retention on the stratum corneum. Pig skin is considered a good mimic for human skin in a variety of applications including penetration studies for chemicals and nanoparticles (Swindle et al., *Veterinary Pathology* 49:738-738 and 344 (2012); Barbero et al., *Toxicol. In Vitro* 23:1-13 (2009)). These results indicate that PLA-HPG$_{ALD}$ NPs exhibit no skin penetration whereas the PLA-HPG NPs exhibit considerable penetration into follicles, reflect the adhesion of PLA-HPG$_{ALD}$ NPs to proteins on the skin surface, which prevents diffusion of nanoparticles to deeper skin layer or into follicles.

Figure 4A:
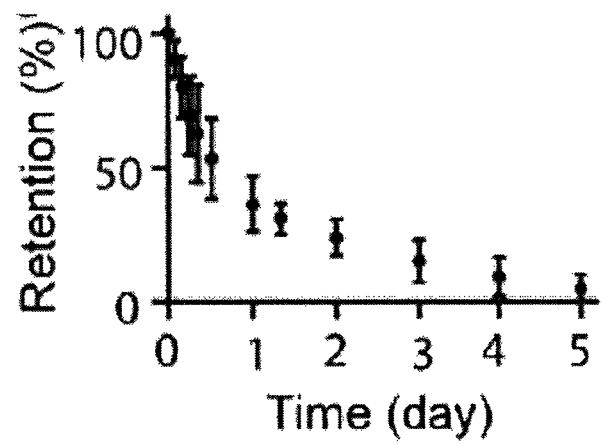
FIG. 4A is a graph showing percent retention (%) of PLA-HPG$_{ALD}$ NPs encapsulating an infrared dye, IR-780, as a function of time (days) following application to the dorsal skin of mice.
Figure 4B:
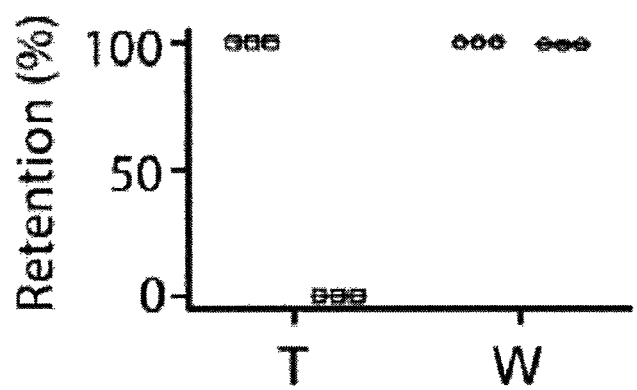
FIG. 4B is a graph showing percent retention (%) of PLA-HPG$_{ALD}$ NPs encapsulating an infrared dye, IR-780, as a function of treatment with towel (T) or water (W). After washing with water or wiping with a wet towel, the PLA-HPG$_{ALD}$ NPs skin retention was imaged with Xenogen. The fluorescence was quantified and normalized to the fluorescence intensity at the starting point.

The water resistance and potential for removal of PLA-HPG$_{ALD}$ NPs by encapsulating an infrared dye, IR-780, into BNPs (0.5% loading), and measuring nanoparticle skin concentrations with in vivo imaging was investigated. The IR-780/PLA-HPG$_{ALD}$ NPs were characterized by TEM and DLS (Table 2). After extensive washing with water, no significant change in fluorescence was observed; however, the PLA-HPG$_{ALD}$ NPs were removed after wiping with a wet towel (FIGS. 4A and 4B). If untreated, PLA-HPG$_{ALD}$ NPs concentration diminished markedly (approximately 75%) within 24 hr and disappearance was essentially complete after five days (FIG. 5A).

These examples show that PLA-HPG$_{ALD}$ NPs will interact with tissues since the bioadhesive property of PLA-HPG$_{ALD}$ NPs is resulted from the Schiff-base bond between the aldehyde groups on PLA-HPG$_{ALD}$ NPs and the amine groups in tissue surface.

These results support the use of PLA-HPG NPs in local delivery where an extended retention at delivery sites is needed. The density of the aldehydes on NPs can be controlled thereby providing tunability in the behavior of the PLA-HPG$_{ALD}$ NPs for local delivery, especially since the PLA-HPG NPs penetrated into hair follicles on the pig skin.

Sunscreens based on PLA-HPG$_{ALD}$ NPs can simplify the current sunscreen formulation as well as eliminate the use of irritants and/or allergens. PLA-HPG$_{ALD}$ NPs are ideal vehicles for sunscreen application since they are water-soluble but their interaction with skin is water-resistant. The PLA-HPG$_{ALD}$ NPs disappear from skin naturally by exfoliation of the stratum corneum; removal can be accelerated mechanically by towel drying. Moreover, nanoparticles, of the size used in this study, yield more transparent suspensions, which may be favored in topical applications for aesthetic reasons.

Example 5. Synthesis of Padimate O (PO)-Loaded PLA-HPG$_{ALD}$ NPs

Materials and Methods

PLA-HPG polymer and PO (an organic compound used in sunscreens), in certain ratio (ratio from 1:1 to 20:1 and total mass of 50-100 mg), were dissolved in 1.5-3.0 ml solvent mixture (Ethyl acetate:DMSO=4:1) was added into 4 ml DI water under vortexing and then subjected to probe sonication for 3 cycles at 10 sec each. The resulting emulsion was diluted in 20 ml DI water with stirring. It was hooked up to a rotovapor to evaporate the ethyl acetate and then applied to an Amico ultra centrifuge filtration unit (100 k cut-off). The PO/PLA-HPG NPs were washed by filtration 2 times then suspended in DI water. The same procedure was implemented to produce PLA-HPG$_{ALD}$ NPs, as PO/PLA-HPG$_{ALD}$ NPs can be oxidized from PO/PLA-HPG NPs nanoparticles.

To quantify the PO loading, the nanoparticles were dissolved in DMSO and the UV absorbance at 310 nm was measured with a plate reader. The amount of PO was calculated by comparing to a reference curve.

Results

All PO/PLA-HPG$_{ALD}$ NPs contained 10% PO. The spherical shape of the PO/BNPs was confirmed by TEM. A hydrodynamic diameter of 138 nm for PO/PLA-HPG$_{ALD}$ NPs was measured by DLS. The results for hydrodynamic diameter of all the NPs generated in these studies are presented in Table 2.

Figure 5:
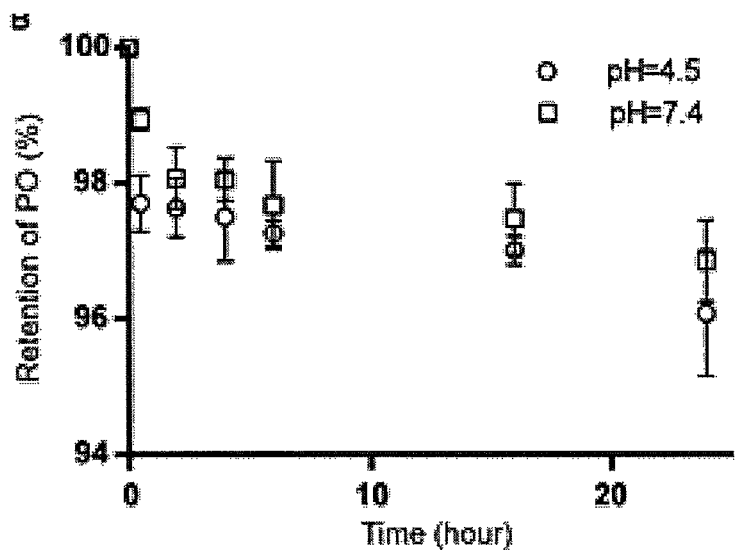
FIG. 5 is a graph showing percent retention of padimate O (PO) (%) within PO/PLA-HPG$_{ALD}$ NPs in releasing medium (containing 0.1% SDS) mimicking the pH range of human sweat as a function of time (hours). Data are shown as mean±SD (n=4).

Example 6. PO-Loaded PLA-HPG$_{ALD}$ NPs Retain PO Under Conditions Mimicking Human Sweat The stability of PO encapsulation in NPs was evaluated by measuring the release of PO in buffer mimicking the pH range (4.5-7.4) of human sweat.
Materials and Methods To quantify PO release from PLA-HPG$_{ALD}$ NPs, a suspension of 1 mg NPs loaded with PO in a dialysis tube (10K cut-off) was dialyzed against 40 ml PBS with 0.1% SDS at 32° C. At each time point, 150 μL solution was removed and 150 μL PBS with 0.1% SDS was added. The amount of released PO was quantified by UV adsorption at 310 nm with a plate reader.
Results The results are shown in FIG. 5. Under conditions mimicking the pH range of human sweat (4.5 and 7.4), PLA-HPG$_{ALD}$ NPs loaded with PO retained more than about 96% of the PO after 20 hours. The particles also exhibited improved UV absorption compared to PO dispersed in water or aqueous buffer.

Example 7. PO-Loaded PLA-HPG$_{ALD}$ NPs Effectively Absorb UV Light and Confine Reactive Oxygen Species Most organic UV filters prevent sunburn by absorbing UV radiation. Therefore, their effectiveness can be estimated by measuring their UV absorption efficiency. Photoinduced changes in UV filters often produce toxic intermediates including ROS that are destructive to multiple cellular components including gDNA (Hanson et al., *Free Radical Biology and Medicine*, 41:1205-1212 (2006)). It has been reported that encapsulating UV filters in polymeric nanoparticles improves filter photostability and delays photodegradation of the UV filters (Perugini et al., *International Journal of Pharmaceutics*, 246:37-45 (2002)). To test whether encapsulating UV-filters in PLA-HPG$_{ALD}$ NPs would in turn confine any generated ROS within the nanoparticles, thereby eliminating potential side-effects, the PO/PLA-HPG$_{ALD}$ NPs and PO suspension were mixed with DHR and exposed to UV. The UV absorption of PO/PLA-HPG$_{ALD}$ NPs was evaluated by measuring their absorption spectrum within the UV range (260-400 nm).
Materials and Methods PO/PLA-HPG$_{ALD}$ NPs suspended in water, PO emulsified in water and PO dissolved in mineral oil at a PO concentration of 0.01 mg/ml were aliquoted into a UV transparent plate and scanned through the UV absorbance spectrum from 260-400 nm with a plate reader. Blank PLA-HPG$_{ALD}$ NPs, water and mineral oil were also scanned as background controls. The PO emulsion in water was made by probe sonication. For the DHR assay, PO/PLA-HPG$_{ALD}$ NPs, PLA-HPG$_{ALD}$ NPs, PO water emulsion at a PO concentration of 0.1 mg/ml was incubated with DHR in 96 well plate. After exposing to UV-B (280-320 nm), plate fluorescence was read at Ex/Em 500/536 nm.

Dihydrarhodamine (DHR), a widely used ROS probe (Hanson et al., *Free Radical Biology and Medicine*, 41:1205-1212 (2006)), was used to detect reactive radicals generated by PO after UV exposure. DHR was mixed with PO/PLA-HPG$_{ALD}$ NPs, emulsified PO, and PLA-HPG$_{ALD}$ NPs separately and exposed to UV. DHR in PBS was used as a control because it absorbs UV at 280-315 nm and becomes fluorescent.

Results

Figure 6A:
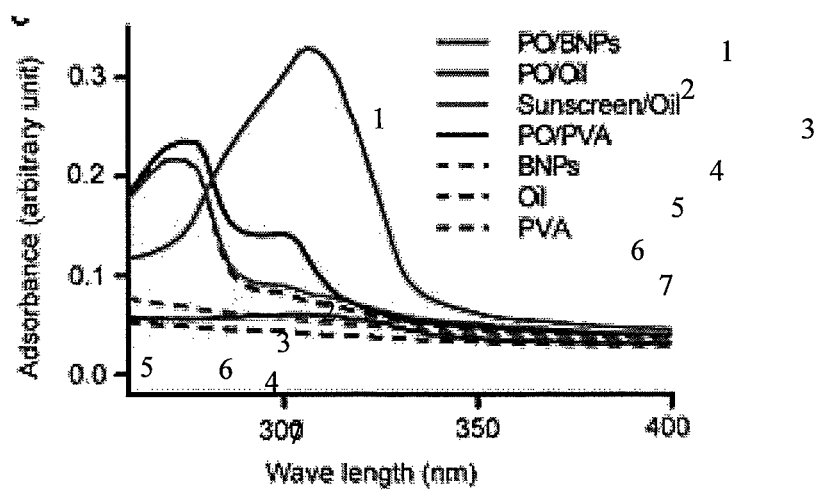
FIGS. 6A and 6B are graphs of 260-400 nm UV light absorbance by PO/PLA-HPG$_{ALD}$ NPs (PO/BNPs, (1)), PO emulsion in PVA solution (PO/PVA, (4)), PO dissolved in mineral oil (PO/Oil, (2)) at a PO concentration of 0.01 mg/ml, sunscreen dissolved in mineral oil (Sunscreen/Oil, (3)) at 0.01 mg/ml plotted without (FIG. 6A) and with (FIG. 6B) background subtraction of blank vehicles (BNPs (5), Oil (6) and PVA (7)). Data are shown as mean (n=4).
Figure 6B:
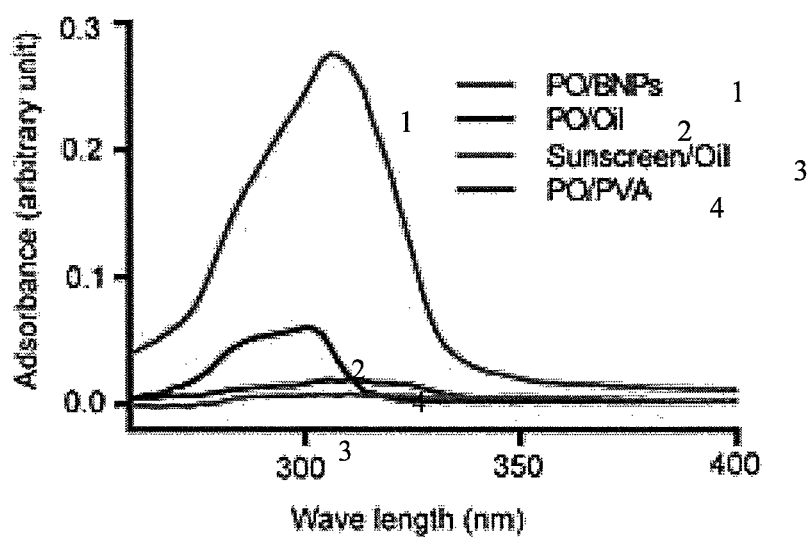

PO/PLA-HPG$_{ALD}$ NPs were compared to PO emulsified in polyvinyl alcohol (PVA) solution (PO/PVA), PO in mineral oil (PO/oil), sunscreen (L'Oreal sunscreen oil spray) in mineral oil (sunscreen/oil); blank PLA-HPG$_{ALD}$ NPs, mineral oil and PVA solution were used as controls (FIG. 6A). All solutions contained equivalent PO concentrations (0.01 mg/ml). PO/PLA-HPG$_{ALD}$ NPs showed a 20-fold higher absorption compared to the PO emulsion in PVA solution and sunscreen diluted in mineral oil (active ingredients adjusted to 0.01 mg/ml) after background subtraction of the appropriate base material (FIG. 6B).

The PO/PVA emulsion is a simplified, representative version of a sunscreen formulation (Allured, *Cosmet Toiletries*, 99:79-79 (1984)); most current sunscreens are based on an emulsion of UV filters (Tanner, *Dermatologic Clinics*, 24:53-62 (2006)). The sunscreen oil used in this example is an oil spray with the same active ingredients and SPF value as the sunscreen lotion used in the animal studies. These results indicate a significant improvement in UV absorption efficiency of PO/PLA-HPG$_{ALD}$ NPs compared to PO dissolved in mineral oil.

Figure 6C:
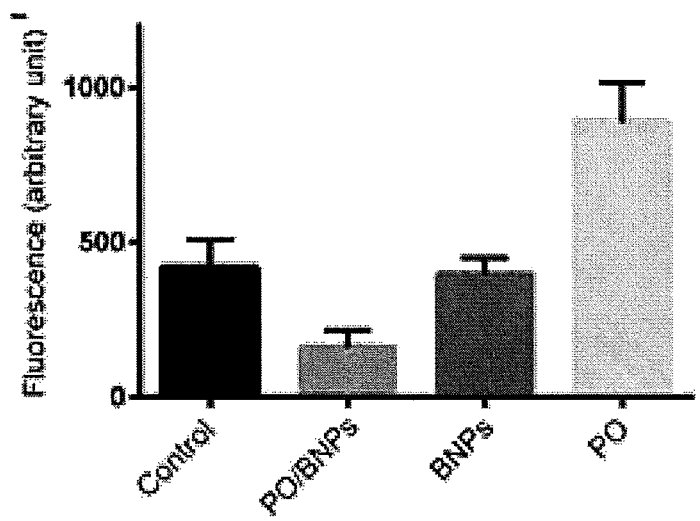
FIG. 6C is a graph showing fluorescence of DHR after DHR was mixed with PO/PLA-HPG$_{ALD}$ NPs (PO/BNPs), blank PLA-HPG$_{ALD}$ NPs (BNPs), PO emulsion (PO) and PBS control (Control) and exposed to UV. Data are shown as mean±SD (n=8). DHR—dihydrorhodamine, BNPs—bioadhesive nanoparticles (PLA-HPG$_{ALD}$ NPs), PO/BNPs—PLA-HPG$_{ALD}$ NPs encapsulating PO, PBS—phosphate buffered saline, PO—padamate O, PVA—polyvinyl alcohol.

The PLA-HPG$_{ALD}$ NPs had a negligible effect on the background fluorescence of DHR as measured by the control since they did not absorb UV. The fluorescence from the PO suspension is much higher than the control (FIG. 6C). It is believed that the free ROS generated from the photoactivated PO after UV exposure oxidized the DHR into fluorescent species. In contrast, by confining the ROS within NPs, the PO/PLA-HPG$_{ALD}$ NPs significantly decreased the background fluorescence.

Example 8. PO-Loaded PLA-HPG$_{ALD}$ NPs Protect Against Sunburn

The protective effect of the PO/PLA-HPG$_{ALD}$ NPs against sunburn on the dorsal skin of Nude mice was evaluated.
Materials and Methods Nude mice were anesthetized with Ketamine/Xylazine, and their dorsal skin was cleaned with 70% alcohol and demarcated into four quadrants. One quadrant was used as a PBS control and other areas were treated with sunscreen, PO/PLA-HPG$_{ALD}$ NPs or blank PLA-HPG$_{ALD}$ NPs.

Only the dorsal epidermis was exposed to the UV lamp (UV-A and UV-B, 280-400 nm, 8 W) for one min (2160 J/m$^2$) and the remaining skin was covered with screens. The mice were left in separate cages and monitored until they woke up. Three days after UV exposure, the dorsal skin was removed and prepared for histology. Images were analyzed for epidermal thickness and keratin content using ImageJ.
Results Three days after UV exposure, skin treated with both PO/PLA-HPG$_{ALD}$ NPs and sunscreen contained no visible erythema, edema or ulceration. However, both skin patches treated with PBS and blank PLA-HPG$_{ALD}$ NPs were damaged considerably by the same UV exposure. A similar pattern of UV toxicity was seen after staining the dorsal skin with hematoxylin and eosin (H&E) (FIG. 7A). There was significant acanthosis with prominent rete ridges present in the unprotected samples, consistent with epidermal hypertrophy, whereas the skin protected by sunscreen or PO/PLA-HPG$_{ALD}$ NPs appeared comparable to normal controls. The UV filter (PO) concentration in PO/PLA-HPG$_{ALD}$ NPs was less than 5% of that contained in the sunscreen, yet the PO/PLA-HPG$_{ALD}$ NPs achieved a similar gross UV protection effect. Trichome staining was also employed to measure the anti-UV effect against sunburn (FIG. 7B). The skin protected by sunscreen showed thickened orthokeratosis, a more subtle epidermal response than to UV-damage, relative to the skin protected by PO/PLA-HPG$_{ALD}$ NPs and the normal skin control. Overproduction of keratin can cause keratosis pilaris, often blocking the opening of hair follicles and resulting in further skin irritation. These results may therefore also demonstrate another non-irritating benefit of sunblock based on PLA-HPG$_{ALD}$ NPs.

Example 9. PO-Loaded PLA-HPG$_{ALD}$ NPs Protect Against DNA Double-Stranded Breaks The ability of the PO/PLA-HPG$_{ALD}$ NPs to protect against DNA double-stranded breaks (DSBs) was evaluated in FVB mice.

Materials and Methods

The dorsal hair of FVB mice was shaved with electric clippers and treated with depilatory cream. One week later, the mice received either PO/PLA-HPG$_{ALD}$ NPs, sunscreen, or no treatment followed by dorsal exposure to UV (160 J/m2) one hour after treatment. For cyclobutane pyrimidine dimers (CPDs) staining, dorsal skin flaps were removed five minutes after UV exposure, and incubated in PBS containing 20 mM EDTA for 2 hours at 37° C. to allow separation of the epidermis from the dermis. The epidermal sheet was then rinsed in PBS, fixed in acetone for 20 min at −20° C., then permeabilized in cold PBS containing 0.5% Triton X-100 for 30 min. Sheets were denatured with 0.4 M NaOH in 70% ethanol for 22 min and then washed with cold PBS containing 0.5% Triton X-100 four times, eight min each. Sheets were blocked with PBS containing 2% BSA, 0.5% Triton-X-100 and 1% goat serum for one hour at room temp, then stained overnight at 4° C. with anti-thymine dimer (2 mg/ml, Abcam#ab10347) and diluted in PBS containing 0.4% BSA and 0.5% Triton X-100.

The remaining steps were carried out at room temperature. Samples were washed in PBS containing 0.5% Triton-X 100 for two hour, stained for two hour with Alexa568-goat-anti-mouse IgG (Invitrogen), washed again, mounted in DAPI (Invitrogen) and examined under a Leica 5P Confocal microscope.

For γH2AX staining, 20 hours after UV exposure, dorsal skin flaps were removed and incubated in 0.5 M ammonium thiocyanate for 20 min at 37° C. to allow for separation of the epidermis from the dermis. The epidermal sheet was then rinsed in PBS, fixed in acetone for 20 min at −20° C., then rehydrated in cold PBS. Sheets were blocked and nuclei were permeabilized in PBS containing 2% BSA and 0.5% Triton-X-100 for one hour at room temp, then stained overnight at 4° C. with anti-γH2AX (1 mg/ml, clone JBW30, Millipore, Billerica, Mass.) and diluted in PBS containing 0.4% BSA and 0.5% Triton X-100.

The remaining steps were carried out at room temperature. Samples were washed in PBS containing 0.5% Triton-X 100 for two hour, stained for two hour with Alexa568-goat-anti-mouse IgG (Invitrogen), washed again, mounted in DAPI (Invitrogen) and examined under a Leica 5P Confocal microscope. For CPD staining, 5 fields/sheet (1 sheet/mouse) were taken using the stage control to move 1 mm between fields in a set pattern. The fluorescence from CPD staining on nuclei was quantified by image J. For γH2AX staining, all of the areas with γH2AX+ cells on a sheet (1 sheet/mouse) were imaged. The γH2AX+ cells were counted using ImageJ particle analyzer software with the threshold set to eliminate the very faint γH2AX staining. The surface concentration of γH2AX+ cells was calculated by dividing the overall number of the γH2AX+ cells on a sheet with the surface area of the sheet.

Results

Both PO/PLA-HPG$_{ALD}$ NPs and sunscreen showed no detectable CPDs, but the positive control (unprotected skin) revealed marked widespread CPD formation after UV exposure (FIG. 8). Even though UV filter content in PO/PLA-HPG$_{ALD}$ NPs was less than 5% of that in sunscreen, it achieved the same level of UV protection.

Figure 9:
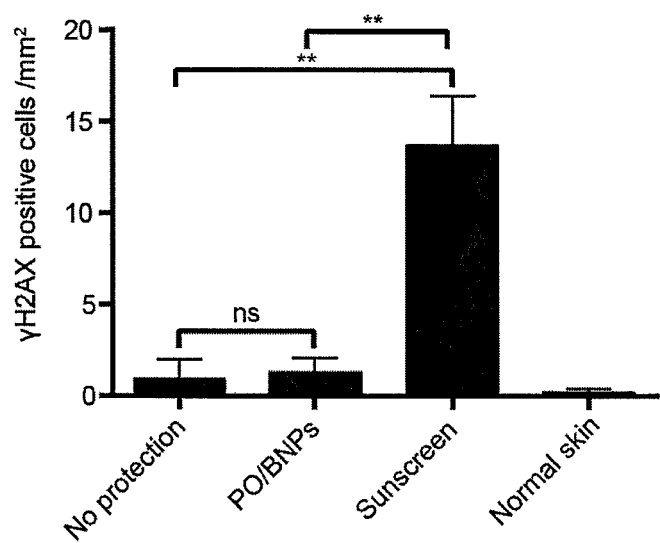
FIG. 9 is a bar graph of γH2AX positive cells per mm$^2$ in mouse dorsal skin sections that received different topical interventions. Skin sections were analyzed 20 hours after exposure to UV-B. The fluorescence of γH2AX on skin after each intervention was quantified. Data are shown as mean±SD (n=3), **p<0.01 (student t-test). BNP—bioadhesive nanoparticles (PLA-HPG$_{ALD}$ NPs), γH2AX—phosphorylated histone H2AX, PO/BNP—bioadhesive nanoparticles (PLA-HPG$_{ALD}$ NPs) encapsulating PO, PO—padamate O.

DSBs induced by UV irradiation are highly carcinogenic. UVB exposure does not directly produce DSBs (Bastien et al., *The Journal of Investigative Dermatology*, 130:2463-2471 (2010)); however, it is possible that UV filters present in the epidermis and dermis can produce ROS after photoactivation, react with cellular DNA, and ultimately produce DSBs (Gulston and Knowland, *Mutat Res-Gen Tox En.* 444:49-60 (1999); Hanson et al., *Free Radical Biology and Medicine*, 41:1205-1212 (2006); Bastien et al., *The Journal of Investigative Dermatology*, 130:2463-2471 (2010); Girard et al., *J Phys Conf Ser.* 261 (2011); Limoli et al., *Proc. Natl. Acad. Sci. U.S.A.* 99:233-238 (2002); Han et al., *Cancer Res.* 64:3009-3013 (2004)). DSBs recruit phosphorylated histone H2A variant H2AX (γH2AX) to the damaged sites (Rogakou et al., *J. Biol. Chem.* 273:5858-5868 (1998)). The group of mice treated with conventional sunscreen showed the highest level of DNA-damage by γH2AX recruitment; in contrast, the level of γH2AX in both the PO/PLA-HPG$_{ALD}$ NPs and non-exposed control were comparable to the normal skin control (FIG. 9).

SUMMARY

Figure 10A:
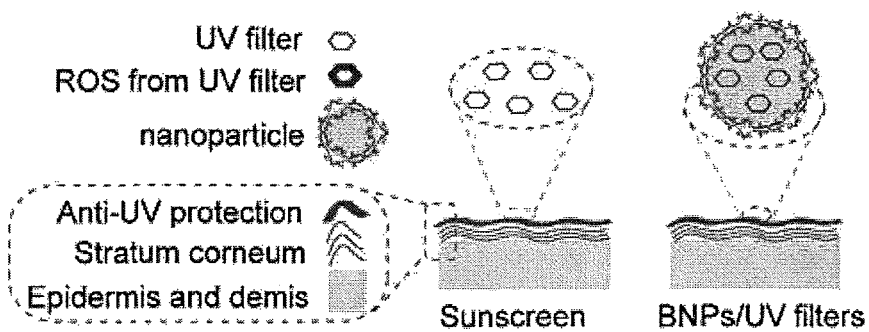
FIGS. 10A, 10B, and 10C are diagrams comparing application of commercial sunscreen (Sunscreen) to PLA-HPG$_{ALD}$ NP (BNPs)-based sunscreen (BNPs/UV filters).
Figure 10B:
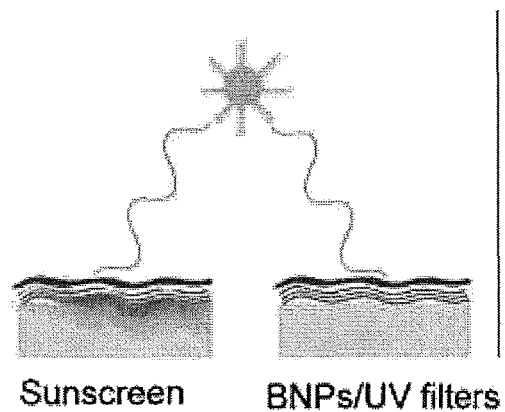
Figure 10C:
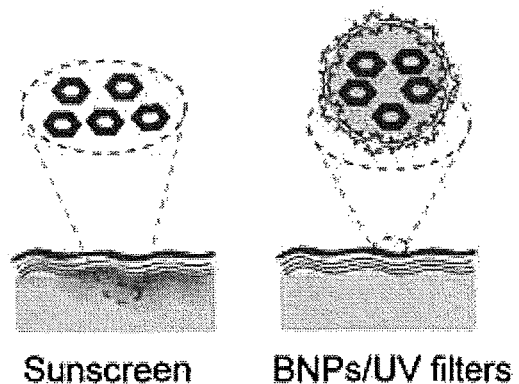

UV exposure from sunlight remains a significant health risk, and there continues to be controversy as to the safety and benefits of commercially available sunscreens. In order to address these issues, a sunblock based on PLA-HPG$_{ALD}$ NPs was developed. FIGS. 10A, 10B, and 10C are diagrams comparing application of commercial sunscreen (Sunscreen) to PLA-HPG$_{ALD}$ NP (BNPs)-based sunscreen (BNPs/UV filters). FIG. 10A is a diagram of sunscreen formulations applied onto the skin. FIG. 10B is a diagram of the skin after application: regular sunscreen penetrates into the skin whereas the PLA-HPG$_{ALD}$ NP (BNPs) formulation remains on the stratum corneum. FIG. 10C is a diagram of the skin after sunlight exposure: UV filters produce deleterious ROS, however, PLA-HPG$_{ALD}$ NPs (BNPs) do not penetrate into the skin and prevent ROS mediated toxicity by confining these toxic products within the particle.

Relative to conventional preparations, the PLA-HPG$_{ALD}$ NPs sunblock demonstrated a durable and specific adherence to the stratum corneum, without any evidence of penetration into cellular components of the epidermis (FIG. 10A); a 20-fold greater UV spectral absorbance; superior protection against UV-induced CPDs and DSBs (FIG. 10B); and improved protection against UV-induced orthokeraosis (FIG. 10C). Additionally, PLA-HPG$_{ALD}$ NPs on skin are water resistant, yet are easily removed with towel drying, or disappear naturally by exfoliation of the stratum corneum. Encapsulating UV filters within BNPs prevented skin exposure to the filter molecules, and the subsequent ROS produced after UV photochemical activation. With less than 5% UV filter encapsulation, the protective effect of PO/PLA-HPG$_{ALD}$ NPs against sunburn was comparable to commercial sunscreen in animal studies, and had the added benefit of preventing subsequent ROS mediated DSBs.

The invention claimed is:

1. Particles comprising a hydrophobic polymer core and a shell comprising hyperbranched polyglycerol covalently bound to the hydrophobic polymer;
   wherein the hyperbranched polyglycerol is functionalized with one or more reactive functional groups or functional groups having tissue targeting moieties bound thereto, wherein the reactive functional groups and the tissue targeting moieties adhere to tissue, cells, or proteins, and
   one or more agents protecting the skin from ultraviolet light, therapeutic agents, diagnostic agents, prophylactic agents, and combinations thereof encapsulated within the particles, associated with the surface of the particles, or combinations thereof.

2. The particles of claim 1, wherein the core comprises a biodegradable hydrophobic polymer.

3. The particles of claim 2, wherein the hydrophobic polymer is selected from the group consisting of polyhydroxyalkanoates, poly(hydroxy acids), polyanhydrides, polyorthoesters, copolymers and blends thereof, poly(lactic acid), poly(glycolic acid), and copolymers thereof.

4. The particles of claim 1 wherein the hyperbranched polyglycerol has tissue targeting moieties bound to the reactive functional groups.

5. The particles of claim 1, wherein the one or more reactive functional groups are selected from the group consisting of aldehydes, amines, O-substituted oximes, and combinations thereof.

6. The particles of any one of claims 1, wherein the one or more agents protect the skin from ultraviolet light.

7. The particles of claim 1, wherein the one or more agents are encapsulated within the particles.

8. The particles of claim 1, wherein the one or more agents are associated with the surface of the particles.

9. The particles of claim 1, wherein the one or more agents are encapsulated within the particles and associated with the surface of the particles.

10. The particles of claim 1, wherein the one or more agents are filters of or block ultraviolet light.

11. The particles of claim 10, wherein the one or more agents are selected from the group consisting of zinc oxide (ZnO), titanium dioxide ($TiO_2$), avobenzone, tinosorb S, mexoryl SX, mexoryl XL, helioplex, octinoxate, octocrylene, oxybenzone, octisalate, homosalate, uvinul T 150, cinoxate, aminobenzoic acid, padimate O, ensulizole, dioxybenzone, meradimate, sulisobenzone, trolamine salicylate, enzacamene, bisdisulizole disodium, uvinul A Plus, uvasorb HEB, parsol SLX, amiloxate, and combination thereof.

12. The particles of claim 1, wherein the average diameter of the particles is from about 1 nm to about 1 mm.

13. The particles of claim 1, comprising a carrier suitable for topical administration.

14. A method for delivering one or more agents blocking ultraviolet light, therapeutic agents, diagnostic agents, prophylactic agents, nutraceuticals, or combinations thereof to the skin of an individual in need thereof, comprising administering an effective amount of the particles of claim 13.

15. The particles of claim 1, wherein the particles are designed to release one or more therapeutic agents, diagnostic agents, prophylactic agents, nutraceuticals, or combinations thereof over a period of hours to weeks.

16. The particles of claim 1, wherein the particles have a density of surface functionality selected from at least 1, 2, 3, 4, 5, 6, or 8 groups/$nm^2$.

17. The particles of claim 1, wherein the particles contain different types of molecules encapsulated within and/or attached to their surface.

18. The particles of claim 1, wherein the particles contain both targeting agents and one or more agents selected from the group consisting of therapeutic agents, diagnostic agents, prophylactic agents and nutraceuticals.

19. The particles of claim 1, wherein the particles are modified to adhere specifically to one or more target molecules associated with a target selected from the group consisting of organs, tissues, cells and extracellular matrix.

20. The particles of claim 1 in a topical formulation for application to the skin, cornea, orifice or mucosa.

21. The particles of claim 20, wherein the particles release different therapeutic agents, diagnostic agents, prophylactic agents, nutraceuticals, or combinations thereof encapsulated within and/or attached to the surface of the particles.

22. The particles of claim 20, wherein the formulation further comprises one or more therapeutic agents, diagnostic agents, prophylactic agents, nutraceuticals, or combinations thereof formulated with the particles.

23. The particles of claim 20, wherein the particles contain different therapeutic agents, diagnostic agents, prophylactic agents, nutraceuticals, or combinations thereof.

24. The particles of claim 20, wherein the particles release different amounts of therapeutic agents, diagnostic agents, prophylactic agents, nutraceuticals, or combinations thereof.

25. The particles of claim 20, wherein the particles release different amounts or different therapeutic agents, diagnostic agents, prophylactic agents, nutraceuticals, or combinations thereof at same time or at different times.

26. The particles of claim 20, wherein the particles comprise a combination of different targeting agents encapsulated within, surrounded by and/or distributed throughout the particles.

* * * * *